United States Patent
Chan et al.

(10) Patent No.: US 6,927,065 B2
(45) Date of Patent: Aug. 9, 2005

(54) METHODS AND APPARATUS FOR CHARACTERIZATION OF SINGLE POLYMERS

(75) Inventors: Eugene Y. Chan, Brookline, MA (US); Lance C. Gleich, Somerville, MA (US); Parris S. Wellman, Hillsborough, NJ (US)

(73) Assignee: U.S. Genomics, Inc., Woburn, MA (US)

( * ) Notice: Subject to any disclaimer, the term of this patent is extended or adjusted under 35 U.S.C. 154(b) by 614 days.

(21) Appl. No.: 09/875,779

(22) Filed: Jun. 6, 2001

(65) Prior Publication Data

US 2002/0039737 A1 Apr. 4, 2002

Related U.S. Application Data

(63) Continuation-in-part of application No. 09/636,793, filed on Aug. 11, 2000, now Pat. No. 6,696,022.
(60) Provisional application No. 60/149,020, filed on Aug. 13, 1999.

(51) Int. Cl.$^7$ .............................................. G01N 21/64
(52) U.S. Cl. ............................ 436/94; 436/56; 436/86; 436/150; 436/164; 436/172
(58) Field of Search ........................... 436/94, 86, 164, 436/172, 56, 150; 435/6

(56) References Cited

U.S. PATENT DOCUMENTS

| | | |
|---|---|---|
| 5,079,169 A | 1/1992 | Chu et al. |
| 5,356,776 A | 10/1994 | Kambara et al. |
| 5,405,747 A | 4/1995 | Jett et al. |
| 5,427,663 A | 6/1995 | Austin et al. |
| 5,538,898 A | 7/1996 | Wickramasinghe et al. |
| 5,599,664 A | 2/1997 | Schwartz |

(Continued)

FOREIGN PATENT DOCUMENTS

| | | |
|---|---|---|
| EP | 0391674 | 10/1990 |
| WO | WO 93/22463 | 11/1993 |
| WO | WO 96/29593 A1 | 9/1996 |
| WO | WO 96/30508 A1 | 10/1996 |
| WO | WO 97/06278 | 2/1997 |
| WO | WO 98/10097 A2 | 3/1998 |
| WO | WO 98/35012 A3 | 8/1998 |
| WO | WO 99/05315 A2 | 2/1999 |
| WO | WO 99/24583 A1 | 5/1999 |
| WO | WO 00/06587 A1 | 2/2000 |
| WO | WO 00/09757 A1 | 2/2000 |
| WO | WO 00/60072 A1 | 10/2000 |
| WO | WO 00/60114 A2 | 10/2000 |
| WO | WO 01/13088 A1 | 2/2001 |

(Continued)

OTHER PUBLICATIONS

Bakajin et al., Electrohydrodynamic stretching of DNA in confined environments. Phys Rev Lett. Mar. 23, 1998; 80(12): 2737–40.

(Continued)

*Primary Examiner*—Jan M. Ludlow
(74) *Attorney, Agent, or Firm*—Wolf, Greenfield & Sacks, PC

(57) ABSTRACT

A method for determining the length and velocity of single elongated macromolecules is disclosed. In particular, the present invention relates to methods and apparatus for determining the velocity of elongated polymeric molecules moving relative to one or more detection stations, as well as to methods and apparatus for determining the length of such molecules and the distance between landmarks that may be present on such molecules. The invention makes use of time correlated measurements of signal amplitude profiles that result from interactions between each detection station and portions of each macromolecule.

24 Claims, 7 Drawing Sheets

U.S. PATENT DOCUMENTS

| | | | |
|---|---|---|---|
| 5,707,797 A | 1/1998 | Windle | |
| 5,795,782 A | 8/1998 | Church et al. | |
| 5,837,115 A | 11/1998 | Austin et al. | |
| 5,840,862 A | 11/1998 | Bensimon et al. | |
| 5,846,724 A | 12/1998 | Bensimon et al. | |
| 5,846,832 A | 12/1998 | Oefner et al. | |
| 5,851,769 A | 12/1998 | Gray et al. | |
| 6,015,714 A | 1/2000 | Baldarelli et al. | |
| 6,210,896 B1 | 4/2001 | Chan | |
| 6,263,286 B1 | 7/2001 | Gilmanshin et al. | |
| 6,355,420 B1 | 3/2002 | Chan | |
| 6,403,311 B1 | 6/2002 | Chan | |
| 6,696,022 B1 | 2/2004 | Chan et al. | |
| 6,762,059 B2 | 7/2004 | Chan et al. | |
| 6,772,070 B2 | 8/2004 | Gilmanshin et al. | |
| 2002/0039737 A1 | 4/2002 | Chan et al. | |
| 2002/0110818 A1 | 8/2002 | Chan | |
| 2002/0119455 A1 | 9/2002 | Chan | |
| 2002/0187508 A1 | 12/2002 | Wong | |
| 2002/0197639 A1 | 12/2002 | Shia et al. | |
| 2003/0059822 A1 | 3/2003 | Chan et al. | |
| 2003/0215864 A1 | 11/2003 | Gilmanshin et al. | |
| 2003/0235854 A1 | 12/2003 | Chan | |
| 2004/0009612 A1 | 1/2004 | Zhao et al. | |
| 2004/0053399 A1 | 3/2004 | Gilmanshin | |
| 2004/0166025 A1 | 8/2004 | Chan et al. | |

FOREIGN PATENT DOCUMENTS

| | | |
|---|---|---|
| WO | WO 02/099398 A1 | 12/2002 |
| WO | WO 02/101095 A1 | 12/2002 |
| WO | WO 02/101353 A2 | 12/2002 |
| WO | WO 03/025540 A2 | 3/2003 |
| WO | WO 03/091455 A1 | 11/2003 |
| WO | WO 03/100101 A1 | 12/2003 |
| WO | WO 2004/007692 A2 | 1/2004 |
| WO | WO 2004/048514 A2 | 6/2004 |
| WO | WO 2004/066185 A1 | 8/2004 |

OTHER PUBLICATIONS

Fisher88, Fisher Scientific catalog (1988), p. 861.

Austin et al., Stretch genes. Physics Today. 1997; 50:32–8.

Austin et al., Electrophoresis and microlithography, Analysis. 1993; 21: 235–8.

Bensimon et al., Stretching DNA with a receding meniscus: Experiments and models. Phys Rev Lett. Jun 5, 1995;74(23):4754–4757.

Bensimon et al., Alignment and sensitive detection of DNA by a moving interface. Science. Sep 30, 1994;265(5181):2096–8.

Bustamante et al., Entropic elasticity of lambda–phage DNA. Science. Sep 9, 1994;265(5178):1599–600.

Chou et al., A microfabricated device for sizing and sorting DNA molecules. Proc Natl Acad Sci U S A. Jan 5, 1999;96(1):11–3.

Chu et al., Laser manipulation of atoms and particles. Science. 1991; 253: 861–6.

Cluzel et al., DNA: an extensible molecule. Science. Feb. 9, 1996;271(5250):792–4.

Deen et al., Analysis of Transport Phenomena, Oxford University Press; NY. 1998: 275–8.

Duke et al., Microfabricated sieve for the continuous sorting of macromolecules. Phys Rev Lett. 1998; 80: 1552–5.

Ertas et al., Lateral separation of macromolecules and polyelectrolytes in microlithographic arrays. Phys Rev Lett. 1998; 80: 1548–51.

Grandbois et al., How strong is a covalent bond? Science. Mar. 12, 1999;283(5408):1727–30.

Harrison et al., Capillary electrophoresis and sample injection systems integrated on a planar glass chip. Anal Chem. 1992; 64: 1926–32.

Hatfield et al., Dynamic properties of an extended polymer in solution. Phys Rev Lett 1999; 82: 3548–51.

Houseal et al., Real–time imaging of single DNA molecules with fluorescence microscopy. Biophys J. Sep 1989;56(3):507–16.

Jacobson et al., Fused quartz substrates for microchip electrophoresis. Anal Chem. 1995; 67: 2059–63.

Kabata et al., Visualization of single molecules of RNA polymerase sliding along DNA. Science. Dec 3, 1993;262(5139):1561–3.

Kim et al., Intermediates in the folding reactions of small proteins. Annu Rev Biochem. 1990;59:631–60. Review.

Lyon et al., Confinement and detection of single molecules in submicrometer channels. Anal Chem. 1997; 69: 3400–5.

Marko et al., DNA under high tension: overstretching, undertwisting, and relaxation dynamics. Physical Rev. 1998; E27:2134–49.

Marko et al., Stretching DNA. Macromolecules. 1995; 28: 8759–70.

Parra et al., High resolution visual mapping of stretched DNA by fluorescent hybridization. Nat Genet. Sep 1993;5(1):17–21.

Perkins et al., Direct observation of tube–like motion of a single polymer chain. Science. May 6, 1994;264(5160):819–22.

Schmalzing et al., DNA sequencing on micrfabricated electrophoretic devices. Anal Chem. 1998; 70: 2303–10.

Schmalzing et al., DNA typing in thirty seconds with a microfabricated device. Proc Natl Acad Sci U S A. Sep 16, 1997;94(19):10273–8.

Schwartz et al., Ordered restriction maps of *Saccharomyces cerevisiae* chromosomes constructed by optical mapping. Science. Oct 1, 1993;262(5130):110–4.

Seiler et al., Planar glass chips for capillary electrophoresis: repetitive sample injection, quantitation and separation efficiency. Anal Chem. 1993; 65: 1481–8.

Smith et al., Single–polymer dynamics in steady shear flow. Science. Mar 12, 1999;283(5408):1724–7.

Smith et al., Response of flexible polymers to a sudden elongational flow. Science. Aug 28, 1998;281(5381):1335–40.

Smith et al., Direct mechanical measurements of the elasticity of single DNA molecules by using magnetic beads. Science. Nov 13, 1992;258(5085):1122–6.

Tan et al., Nanoscale imagin and sensing by near–field optics. in *Fluorescence Imaging: Spectroscopy and Microscopy*. Wang and Herman, Eds., Chemical Analysis Series 137: 407–75.

Volkmuth et al., DNA electrodiffusion in a 2D array of posts. Phys Rev Lett. 1994: 72: 2117–20.

Volkmuth et al., DNA electrophoresis in microlithographic arrays. Nature. Aug 13, 1992;358(6387):600–2.

Washizu et al., Applications of electrostatic stretch–and–positioning of DNA. IEEE Trans Industry Applications. 1990; 26: 1165–72.

Woolley et al., Ultra–high–speed DNA fragment separations using microfabricated capillary array electrophoresis chips. Proc Natl Acad Sci U S A. Nov 22, 1994;91(24):11348–52.

Zimmermann et al., DNA stretching on functionalized gold surfaces. Nucleic Acids Res. Feb 11, 1994;22(3):492–7.

Akerman, B. et al., "Electrophoretic Orientation of DNA detected by Linear Dichroism Spectroscopy", *J. Chem. Soc. D. Chem. Commun.*, 1985, pp. 422–423.

Allen, M.J. et al., "Scanning Tunneling Microscope Images of Adenine and Thymine at Atomic Resolution", *Scanning Microscopy*, 1991, pp. 625–630, vol. 5, No. 3, Scanning Microscopy International, Chicago.

Ambrose, W.P. et al., "Application of Single Molecule Detection to DNA Sequencing and Sizing", *Ber. Bunsenges. Phys. Chem.*, 1993, pp. 1535–1542, vol. 97, No. 12, VCH Verlagsgesellschaft mbH.

Bello, M.S. et al., "Electroosmosis of polymer in fused silica capillaries", *Electrophoresis*, 1994, pp. 623–626, vol. 15, VCH Verlagsgesellschaft mbH.

Bezrukov, S.M. et al., "Counting polymers moving through a single ion channel", *Nature*, Jul. 28, 1994, pp. 279–281, vol. 370.

Bezrukov, S.M. et al., "The charge state of an ion channel controls neutral polymer entry into its pore", *Eur. Biophys. J.*, 1997, pp. 471–476, vol. 26, Springer–Verlag.

Bustamante, C., "Direct Observation and Manipulation of Single DNA Molecules Using Fluorescence Microscopy", *Annu. Rev. Biophys. Biophys. Chem.*, 1991, pp. 415–446, vol. 20, Annual Reviews, Inc.

Cantor, C.R. et al., "Meeting Report—Report on the Sequencing by Hybridization Workshop", *Genomics*, 1992, pp. 1378–1383, vol. 13, Academic Press, Inc.

Castro, A. et al., "Single–Molecule Electrophoresis", *Analytical Chemistry*, Sep. 15, 1995, pp. 3181–3186, vol. 67, No. 18.

Chen, D. et al., "Single–Molecule Detection in Capillary Electrophoresis: Molecular Shot Noise as a Fundamental Limit to Chemical Analysis", *Anal. Chem.*, Feb. 15, 1996, pp. 690–696, vol. 68, No. 4.

Church, G.M. et al., "Multiplex DNA Sequencing", *Science*, Apr. 8, 1988, pp. 185–191, vol. 240.

Clegg, R.M., "Fluorescence resonance energy transfer", *Current Opinion in Biotechnology*, 1995, pp. 103–110, vol. 6, Current Biology LTD.

Davis, L.M. et al., "Rapid DNA Sequencing Based on Single–Molecule Detection", *Los Alamos Science*, 1992, pp. 280–286, vol. 20.

Drmanac, R. et al., "Sequencing of Magabase Plus DNA by Hybridization: Theory of the Method", *Genomics*, 1989, pp. 114–128, vol. 4, Academic Press, Inc.

Eigen, M. et al., "Sorting single molecules: Application to diagnostics and evolutionary biotechnology", *Proc. Natl. Acad. Sci. USA*, Jun. 1994, pp. 5740–5747, vol. 91.

Fan, F.R.F. et al., "Electrochemical Detection of Single Molecules", *Science*, Feb. 10, 1995, pp. 871–874, vol. 267.

Gadella, T.W.J. et al., "Fluorescence lifetime imaging microscopy (FLIM): Spatial resolution of microstructures on the nanosecond time scale", *Biophysical Chemistry*, 1993, pp. 221–239, vol. 48, Elsevier Science Publishers B.V. Amsterdam.

Glazer, A.N. et al., "Energy–transfer fluorescent reagents for DNA analyses", *Curr. Opin. Biotechnol.*, Feb. 1997, pp. 94–102, vol. 8, No. 1.

Goodwin, P.M. et al., "Spatial Dependence of the Optical Collection Efficiency in Flow Cytometry", *Cytometry*, 1995, pp. 133–144, vol. 21, Wiley–Liss, Inc.

Gurrieri, S. et al., "Imaging of Kinked Configurations of DNA Molecules Undergoing Orthogonal Field Alternating Gel Electrophoresis by Fluorescence Microscopy", *Biochemistry*, 1990, pp. 3396–3401, vol. 29, American Chemical Society.

Haab, B.B. et al., "Single Molecule Fluorescence Burst Detection of DNA Fragments Separated by Capillary Electrophoresis", *Analytical Chemistry*, Sep. 15, 1995, pp. 3253–3260, vol. 67, No. 18.

Harding, J.D. et al., "Single–molecule detection as an approach to rapid DNA sequencing", *Trends in Biotechnology*, Jan.–Feb. 1992, pp. 55–57, vol. 10, Elsevier Science Publishers Ltd. (UK).

Holzwarth, A.R., "Time–Resolved Fluorescence Spectroscopy", *Methods in Enzymology*, 1995, pp. 334–362, vol. 246, Academic Press, Inc.

Holzwarth, G. et al., "The Acceleration of Linear DNA During Pulsed–Field Gel Electrophoresis", *Biopolymers.*, Jun. 1989, pp. 1043–1058, vol. 28, No. 6.

Houseal, T.W. et al., "Real–time imaging of single DNA molecules with fluorescence microscopy", *Biophys. J.*, Sep. 1989, pp. 507–516, vol. 56, Biophysical Society.

Jett, J.H. et al., "High–Speed DNA Sequencing: An Approach Based Upon Fluorescence Detection of Single Molecules", *Journal of Biomolecular Structure & Dynamics*, 1989, pp. 301–309, vol. 7, No. 2, Adenine Press.

Kasianowicz, J.J. et al., "Characterization of individual polynucleotide molecules using a membrane channel", *Proc. Natl. Acad. Sci. USA*, Nov. 1996, pp. 13770–13773, vol. 93.

Kasianowicz, J.J., "Polymer Transport in the Alpha–Hemolysin Ion Channel 6", Abstract, p. 111.

Kinjo, M. et al., "Ultrasensitive hybridization analysis using fluorescence correlation spectroscopy", *Nucleic Acid Research*, 1995, pp. 1795–1799, vol. 23, No. 10, Oxford University Press.

KIVA Genetics Web Page, Printout.

Klenchin, V.A. et al., "Electrically induced DNA uptake by cells is a fast process involving DNA electrophoresis", *Biophys. J.*, Oct. 1991, pp. 804–811, vol. 60, Biophysical Society.

Lee, N. et al., "Diffusion of a Polymer Chain through a Thin Membrane", *J. Phys. II France*, Feb. 1996, pp. 195–204, vol. 6, Les Editions de Physique.

Lee, Y.H. et al., "Laser–Induced Fluorescence Detection of a Single Molecule in a Capillary", *Analytical Chemistry*, Dec. 1, 1994, pp. 4142–4149, vol. 66, No. 23, American Chemical Society.

Lewotsky, K., "Hyperspectral Imaging: evolution of imaging spectrometry", *SPIE OE/Rep.*, Nov. 1994, pp. 1–3.

Little, D.P. et al., "Rapid Sequencing of Oligonucleotides by High–Resolution Mass Spectrometry", *J. Am. Chem. Soc.*, 1994, pp. 4893–4897, vol. 116, No. 11.

Lockhart, D.J. et al., "Expression monitoring by hybridization to high–density oligonucleotide arrays", *Nature Biotechnology*, Dec. 1996, pp. 1675–1680, vol. 14.

Marra, M. et al., End Sequence Determination from Large Insert Clones Using Energy Transfer Fluorescent Primers, *Genome Research*, 1996, pp. 1118–1122, vol. 6, No. 11, Cold Spring Harbor Laboratory Press.

Maxam, A.M. et al., "A new method for sequencing DNA", *Proc. Natl. Acad. Sci. USA*, Feb. 1977, pp. 560–564, vol. 74, No. 2.

Meng, X. et al., "Inhibition of Restriction Endonuclease Activity by DNA Binding Fluorochromes", *Dynamics,* 1996, pp. 945–951, vol. 13, No. 6, Adenine Press.

Mertz, J. et al., "Single–molecule detection by two–photon–excited fluorescence", *Optics Letters,* Dec. 15, 1995, pp. 2532–2534, vol. 20, No. 24, Optical Society of America.

Meinkoth, J. et al., "Nick Translation", *Methods in Enzymology,* 1987, pp. 91–93, vol. 152, Academic Press, Inc.

Metzger, R.A., Article from *Wired,* Nov. 1998, p. 4.

Miki, M. et al., "Kinetics of Structural Changes of Reconstituted Skeletal Muscle Thin Filaments Observed by Fluorescence Resonance Energy Transfer", *The Journal of Biological Chemistry,* Apr. 5, 1993, pp. 7101–7106, vol. 268, No. 10, The American Society for Biochemistry and Molecular Biology, Inc.

Moore, D.P. et al., "The Orientation, Relaxation and Reptation of DNA in Orthogonal Field, Alternatively–Pulsed Gel Electrophoresis (OFAGE): A Linear Dichroism Study", *Biophysical J.,* 1986, p. 130a, vol. 49.

Morikawa, K. et al., "Visualization of Individual DNA Molecules in Solution by Light Microscopy: DAPI Staining Method", *J. Biochem.,* 1981, pp. 693–696, vol. 89, No. 2.

Morozov, V.N. et al., "New polyacrylamide gel–based methods of sample preparation for optical microscopy: immobilization of DNA molecules for optical mapping", *Journal of Microscopy,* Sep. 1996, pp. 205–214, vol. 183, Pt. 3, The Royal Microscopical Society.

Naktinis, V. et al., "A Molecular Switch in a Replication Machine Defined by an Internal Competition for Protein Rings", *Cell,* Jan. 12, 1996, pp. 137–145, vol. 84, Cell Press.

Nie, S. et al., "Probing Individual Molecules with Confocal Fluorescence Microscopy", *Science,* Nov. 11, 1994, pp. 1018–1021, vol. 266.

Nguyen, D.C. et al., "Detection of Single Molecules of Phycoerythrin in Hydrodynamically Focused Flows by Laser–Induced Fluorescence", *Anal. Chem.,* Sep. 1, 1987, pp. 2158–2161, vol. 59, No. 17.

Oida, T. et al., "Fluorescence lifetime imaging microscopy (flimscopy), Methodology development and application to studies of endosome fusion in single cells", *Biophys. J.,* Mar. 1993, pp. 676–685, vol. 64, Biophysical Society.

Pap, E.H.W. et al., "Quantitation of the Interaction of Protein Kinase C with Diacylglycerol and Phosphoinositides by Time–Resolved Detection of Resonance Energy Transfer", *Biochemistry,* 1993, pp. 13310–13317, vol. 32, No. 48.

Parsegian, V.A. et al., "Watching Small Molecules Move: Interrogating Ionic Channels Using Neutral Solutes", *Bioscience Reports,* 1995, pp. 503–514, vol. 15, No. 6, Plenum Publishing Corp.

Peck, K. et al., "Single–molecule fluorescence detection: Autocorrelation criterion and experimental realization with phycoerythrin", *Proc. Natl. Acad. Sci. USA,* Jun. 1989, pp. 4087–4091, vol. 86.

Perisamy, A. et al., "Computerized Fluorescence Microscopic Vision in the Biomedical Sciences", *Journal of Computer–Assisted Microscopy,* 1994, pp. 1–26, vol. 6, No. 1, Plenum Publishing Corp.

Priore, D.R.C. et al., "Comparisons Between Oriented Film and Solution Tertiary Structure of Various Nucleic Acids", *Biopolymers,* 1979, pp. 1809–1820, vol. 18, John Wiley & Sons, Inc.

Rampino, N.J. et al., "Apparatus for Gel Electrophoresis with Continuous Monitoring of Individual DNA Molecules by Video Epifluorescence Microscopy", *Analytical Biochemistry,* 1991, pp. 278–283, vol. 194, Academic Press, Inc.

Reddick, R.C. et al., "New form of scanning optical microscopy", *Physical Review B,* Jan. 1, 1989, pp. 767–770, vol. 39, No. 1.

Rodgers, M.A.J. et al., "Instrumentation for Fluorescence Microscopy with Picosecond Time Resolution", *Photochemistry and Photobiology,* 1985, pp. 613–616, vol. 42, No. 5, Pergamon Press Ltd.

Ronaghi, M. et al., "Real–Time DNA Sequencing Using Detection of Pyrophospate Release", *Analytical Biochemistry,* 1996, pp. 84–89, vol. 242, Academic Press, Inc.

Ross, P.D. et al., "Electrophoresis of DNA. III. The Effect of Several Univalent Electrolytes on the Mobility of DNA," *Biopolymers,* 1964, pp. 231–236, vol. 2.

Saha, A.K. et al., "Time–Resolved Fluorescence of a New Europium Chelate Complex: Demonstration of Highly Sensitive Detection of Protein and DNA Samples" *J. Am. Chem. Soc.,* 1993, pp. 11032–11033, vol. 115, No. 23, American Chemical Society.

Sahota, R.S. et al., "Nonaqueous Capillary Electrophoresis", *Anal. Chem.,* Apr. 1, 1994, pp. 1141–1146, vol. 66, No. 7.

Saiki, R.K. et al., "Primer–Directed Enzymatic Amplification of DNA with a Thermostable DNA Polymerase", *Science,* Jan. 29, 1988, pp. 487–491, vol. 239.

Sanger, F. et al., "DNA sequencing with chain–terminating inhibitors", *Proc. Natl. Acad. Sci. USA,* Dec. 1977, pp. 5463–5467, vol. 74, No. 12.

Schellman, J. et al., "Optical Spectroscopy of Oriented Molecules", *Chem. Rev.,* 1987, pp. 1359–1399, vol. 87, American Chemcial Society.

Schwartz, D.C. et al., "Conformational dynamics of individiual DNA molecules during gel electrophoresis", *Nature,* Apr. 6, 1989, pp. 520–522, vol. 338.

Selvin, P.R. et al., "Luminescence Resonance Energy Transfer", *J. Am. Chem. Soc.,* 1994, pp. 6029–6030, vol. 116, American Chemical Society.

Shera, E.B. et al., "Detection of single fluorescent molecules", *Chemical Physics Letters,* Nov. 23 1990, pp. 553–557, vol. 174, No. 6, Elsevier Science Publishers B.V. (North–Holland).

Smirnov, I.P. et al., "Sequencing Oligonucleotides by Exonuclease Digestion and Delayed Extraction Matrix–Assisted Laser Desorption Ionization Time–of–Flight Mass Spectrometry", *Analytical Biochemistry,* 1996, pp. 19–25, vol. 238, Academic Press, Inc.

Smith, L.M. et al., "Fluorescence detection in automated DNA sequence analysis", *Nature,* Jun. 12, 1986, pp. 674–679, vol. 321.

Smith, S.B. et al., "Observation of Individual DNA Molecules Undergoing Gel Electrophoresis", *Science,* Jan. 13, 1989, pp. 203–206, vol. 243.

Soper, S. A. et al., "Sanger DNA–Sequencing Reactions Performed in a Solid–Phase Nanorector Directly Coupled to Capillary Gel Electrophoresis", *Analytical Chemistry,* Oct. 1, 1998, pp. 4036–4043, vol. 70, No. 19, American Chemical Society.

Soper, S.A. et al., "Nanoliter–scale sample preparation methods directly coupled to polymethylmethacrylate–based microchips and gel–filled capillaries for the analysis of oligonucleotides", *Journal of Chromatography A*, 1999, pp. 107–120, vol. 853, Elsevier Science B.V.

Sturm, J. et al., "Direct Observation of DNA Chain Orientation and Relaxation by Electric Birefringence: Implications for the Mechanism of Separation during Pulsed–Field Gel Electrophoresis", *Physical Review Letters*, Mar. 27, 1989, pp. 1484–1487, vol. 62, No. 13, The American Physical Society.

Sung, W. et al., "Polymer Translocation through a Pore in a Membrane", *Physical Review Letters*, Jul. 22, 1996, pp. 783–786, vol. 77, No. 4, The American Physical Society.

Taylor, D.L. et al., "Chapter 13. Basic Fluorescence Microscopy", *Methods in Cell Biology*, 1989, pp. 207–237, vol. 29, Academic Press, Inc.

Taylor, D.L. et al., "Detection of Actin Assembly by Fluorescence Energy Transfer", *The Journal of Cell Biology*, May 1981, pp. 362–367, vol. 89, The Rockefeller University Press.

Waggoner, A., "Covalent Labeling of Proteins and Nucleic Acids with Fluorophores", *Methods Enzymol.*, 1995, pp. 362–373, vol. 246, Academic Press, Inc.

Wang, X.F. et al., "Time–Resolved Fluorescence Microscopy Using Multichannel Photon Counting", *Applied Spectroscopy*, 1990, pp. 25–30, vol. 44, No. 1, Society for Applied Spectroscopy.

Wang, Y. et al., "Rapid Sizing of Short Tandem Repeat Alleles Using Capillary Array Electrophoresis and Energy–Transfer Fluorescent Primers", *Anal. Chem.*, Apr. 1, 1995, pp. 1197–1203, vol. 67, No. 7.

Wang, Y. et al., "High–resolution capillary array electrophoretic sizing of multiplexed short tandem repeat loci using energy–transfer fluorescent primers", *Electrophoresis*, 1996, pp. 1485–1490, vol. 17, VCH Verlagsgesellschaft mbH.

Ward, D.C. et al., "Fluorescence Studies of Nucleotides and Polynucleotides. I. Formycin, 2–Aminopurine Riboside, 2,6–Diaminopurine Riboside and Their Derivatives", *The Journal of Biological Chemistry*, Mar. 10, 1969, pp. 1228–1237, vol. 244, No. 5, USA.

Wiemann, S. et al., "Primer Design for Automated DNA Sequencing Utilizing T7 DNA Polymerase and Internal Labeling with Fluorescein–15–dATP", *BioTechniques*, Apr. 1995, pp. 688–697, vol. 18, No. 4.

Wittwer, C.T. et al., "Continuous Fluorescence Monitoring of Rapid Cycle DNA Amplification", *BioTechniques*, Jan. 1997, pp. 130–138, vol. 22, No. 1.

Woolley, A.T. et al., "Ultra–High–Speed DNA Sequencing Using Capillary Electrophoresis Chips", *Anal. Chem.*, Oct. 15, 1995, pp. 3676–3680, vol. 67, No. 20, American Chemical Society.

Wu, J.Y. et al., "Chapter 30. Fast Multisite Optical Measurement of Membrane Potential", Department of Physiology, Yale University School of Medicine, New Haven, CT USA, pp. 389–404.

Wu, P. et al., "Resonance Energy Transfer: Methods and Applications", *Anal. Chem.*, 1994, pp. 1–13, vol. 218, Academic Press, Inc.

Zweig, A., "Photochemical Generation of Stable Fluorescent Compounds (Photofluorescence)", *Pure and Applied Chemistry*, 1973, pp. 389–410, vol. 33.

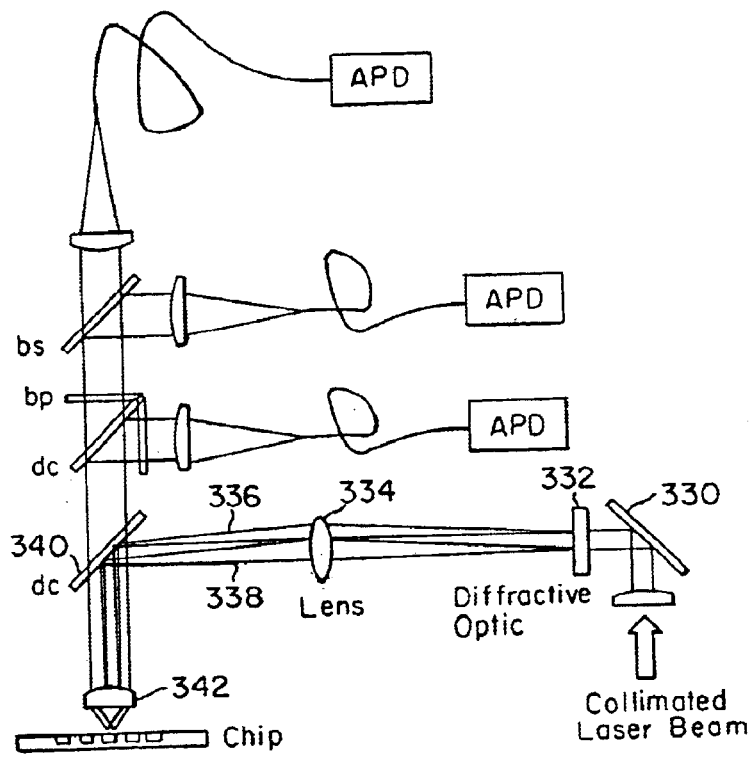
Fig. 8
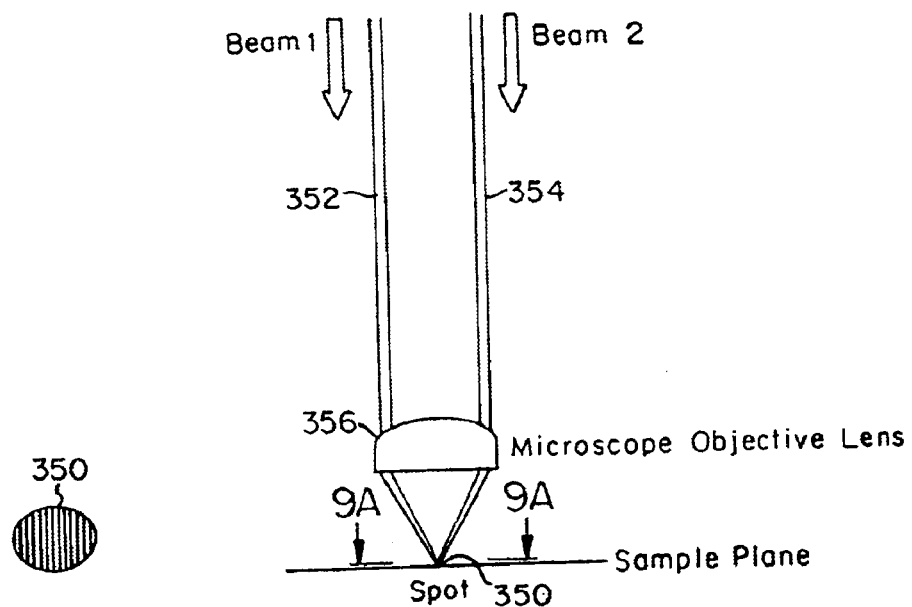
Fig. 9A
Fig. 9

METHODS AND APPARATUS FOR CHARACTERIZATION OF SINGLE POLYMERS

This application is a continuation-in-part of U.S. patent application Ser. No. 09/636,793, filed Aug. 11, 2000 now U.S. Pat. No. 6,696,022, which claims the benefit of U.S. Provisional Application Ser. No. 60/149,020, filed Aug. 13, 1999, each of which is incorporated herein by reference in its entirety.

FIELD OF THE INVENTION

The present invention relates generally to the field of molecular analysis and characterization. More particularly, the present invention relates to methods and apparatus for determining the velocity of elongated polymeric molecules moving relative to a detection station, as well as to methods and apparatus for determining the length of such molecules and the distance between landmarks present on such molecules.

BACKGROUND OF THE INVENTION

Analysis of the structure and dynamics of single macromolecules in a fluid sample has attracted considerable interest due in part to the rapid development of methodologies for the manipulation and detection of single macromolecules. For example, recent developments in experimental techniques and available hardware have increased dramatically the sensitivity of detection so that optical detection can be made of single dye molecules in a sample. Single dye detection can be done in an aqueous solution, at room temperature (see, e.g., Weiss, 1999, Science 283: 1676–1683), and in very small volumes to reduce background. Such single-molecule based analytical methods are especially useful in the analysis of biological macromolecules, such as nucleic acid molecules and proteins. Single-molecule analytical methods require small amounts of sample, thereby alleviating tedious efforts in generating large amounts of sample material. For example, single-molecule analytical methods may allow analysis of the structure of nucleic acid molecules without amplification, e.g., by polymerase-chain reaction (PCR). Single-molecule analytical methods also allow analysis of individual molecules, and are thus particularly useful in the identification of structural and/or dynamical features without the effect of averaging over a heterogeneous population.

A single-molecule electrophoresis (SME) method which combines single molecule detection and electrophoresis has been reported for the detection and identification of single molecules in solution (Castro and Shera, 1995, Anal. Chem. 67: 3181–3186). In SME, sizing of single molecules is accomplished through determination of electrophoretic velocities by measuring the time required for individual molecules to travel a fixed distance between two laser beams. This method has been applied to DNA, to fluorescent proteins and to simple organic fluorophores. For example, SME offers a single-molecule method for sizing of DNA restriction fragments. However, SME detects only the presence or absence of a molecule. The method does not provide information regarding the internal structure of a molecule.

A single-molecule DNA sizing method using a microfabricated device has also been reported (Chou et al., 1999, Proc. Natl. Acad. Sci. USA 96:11–13). The method makes use of the fact that the amount of intercalated dye is proportional to the length of the molecule, and determines the lengths of single DNA molecules by measuring the total fluorescence intensity of DNA stained with intercalating dye molecules. Thus, the method does not use electrophoretic mobilities to determine sizes of molecules. This method also does not provide information regarding the internal structure of a molecule.

PCT Publication No. WO 98/10097 discloses a method and apparatus for detection of single molecules emitting two-color fluorescence and determination of molecular weight and concentration of the molecules. The method involves labeling of individual molecules with at least two fluorescent probes of different emission spectra. Simultaneous detection of the two labels indicates the presence of the molecule. The velocity of the molecule is determined by measuring the time required for the molecules to travel a fixed distance between two laser beams. Comparison of the molecule's velocity with that of standard species permits determination of the molecular weight of the molecule, which may be present in a concentration as small as one femtomolar.

Other techniques for characterizing single macromolecules include a method described in U.S. Pat. No. 5,807,677 for direct identification of a specific target nucleic acid sequence having a low copy number in a test solution. This method involves the preparation of a reference solution of a mixture of different short oligonucleotides. Each oligonucleotide includes a sequence complementary to a section of the target sequence and is labeled with one or more fluorescent dye molecules. The reference solution is incubated with the test solution under conditions favorable to hybridization of the short oligonucleotides with the nucleic acid target. The target sequence is identified in the solution by detection of the nucleic acid strands to which one or more of the labeled oligonucleotides are hybridized. To amplify the fluorescence signal, a "cocktail" of different oligonucleotides is used. In this cocktail, the oligonucleotides are capable of hybridizing with sequences adjacent to but not overlapping with the target sequence. The disadvantage of this method is that, in order to design probes of the proper sequence, the exact sequence of the target nucleic acid and surrounding sequences must be known. A method described in U.S. Pat. No. 5,599,664 and European Patent No. EP 0391674 allows sizing of DNA molecules by first subjecting a DNA molecule to a force such that the DNA molecule is elongated and then measuring the conformational relaxation dynamics. In another method (Schmalzing et al., 1998, Analytical Chemistry 70:2303–2310; Schmalzing et al, 1997, Proc. Natl. Acad. Sci. USA 94:10273–10278), microfabricated devices for DNA analysis were developed, including sequencing, which employ small-scale versions of traditional techniques, such as electrophoresis.

None of these single molecule analytical methods allows the determination of the internal structure of the molecule. A challenge to the characterization of the internal structure, e.g., the linear sequence of monomers, in a single polymer chain is the natural tendency of polymers in most media to adopt coiled conformations. The average degree of such coiling is dependent on, inter alia, the interaction of the polymer with the surrounding solution, the rigidity of the polymer, and the energy of interaction of the polymer with itself. In most cases, the coiling is quite significant. For example, a λ-phage DNA, with a B-form contour length of about 16 $\mu$m long, has a random coil diameter of approximately 1 $\mu$m in water (Smith et al., 1989, Science 243:203–206).

Methods of elongating DNA molecules by fluid flow have been reported (Perkins et al. Science 276:2016–2021; Smith et al., Science 283:1724–1727). In one method, DNA molecules are stretched by an elongational flow. The probability distribution of molecular extension was determined as a function of time and strain rate. Detailed dynamics of elongated DNA molecules in elongational flow has also been observed. In another method DNA molecules are stretched by a steady shear flow. The probability distribution for the molecular extension was determined as a function of shear rate. It was found that, in contrast to the behavior in pure elongational flow, the average polymer extension in shear flow does not display a sharp coil-stretch transition.

DNA has also been stretched by electrophoresis as part of a near-field detection scheme for sequencing biomolecules. DNA has been elongated by electrophoresis both in a gel and in solution, using electrical forces to move the DNA in position for reading (U.S. Pat. No. 5,538,898). However, no data were given to determine the quality of the stretching of large polymers, and the technique is limited to analyzing approximately 3 megabases at a time.

Gravitational forces have also been used to stretch DNA (U.S. Pat. No. 5,707,797; Windle (1993) Nature Genetics 5:17–21). In this technique, drops of DNA from the sodium dodecyl sulfate lysing of cells were allowed to run down a slide held at an angle. The effect of gravity was enough to stretch out the DNA, even to its over-stretched S-DNA form. The DNA was then immobilized on the slide, making processing, e.g., fluorescent labeling, prior to stretching relatively difficult.

Single-molecule DNA analytical methods which involve elongation of DNA molecule include optical mapping (Schwartz et al., 1993, Science 262:110–113; Meng et al., 1995, Nature Genet. 9:432; Jing et al., Proc. Natl. Acad. Sci. USA 95:8046–8051) and fiber-fluorescence in situ hybridization (fiber-FISH) (Bensimon et al., Science 265:2096; Michalet et al., 1997, Science 277:1518). In optical mapping, DNA molecules are elongated in a fluid sample and fixed in the elongated conformation in a gel or on a surface. Restriction digestions are then performed on the elongated and fixed DNA molecules. Ordered restriction maps are then generated by determining the size of the restriction fragments. In fiber-FISH, DNA molecules are elongated and fixed on a surface by molecular combing. Hybridization with fluorescently labeled probe sequences allows determination of sequence landmarks on the DNA molecules. Both methods require fixation of elongated molecules so that molecular lengths and/or distances between markers can be measured.

A method for measuring the length and distances between markers on DNA was developed by Kambara et al. (U.S. Pat. No. 5,356,776). This method involves fluorescently labeling a DNA molecule at both termini and/or internal sites, and moving the labeled molecule through a gel via electrophoresis. In so doing, the DNA molecule is forced into a straightened conformation. The straightened DNA molecule is transferred into a gel-free buffer, and the fluorescent labels are detected. The time interval between the detection of the two labels is used to determine the distance between them. If the two labels label the termini of the DNA molecule, the distance between the labels measures the length of the molecule. The method, which does not provide means for determining the velocity of the DNA molecule, relies on estimating the velocity of DNA from the migration rate of the DNA molecule.

Flow based single-molecule analytical methods for elongation and characterization of single macromolecules have not been widely adopted due in part to the difficulty in precise measurement of molecular characteristics, e.g., the length of the macromolecule, the distance between two landmarks on a macromolecule, etc. For example, to determine the length of an elongated macromolecule as it travels through a detection zone, e.g., a laser excitation zone, it is necessary to know the velocity of the macromolecule. The flow velocity field can be measured by various known methods, e.g., particle image velocimetry (PIV) (see, e.g., Meinhart et al., 1999, Experiments in Fluids 27: 414–419; Meinhart et al., 2000, Meas. Sci. Technol. 11:809–814). The velocities of flexible objects, such as elongated polymers, may not be the same as the flow velocities. For example, in most flows the length of a polymer may be changing as it travels along with flow. In particular, the length of a polymer may be changing as a consequence of changing flow velocity. There is therefore a need for faster, simpler, more reliable and more universally applicable methods for measuring the velocities of single elongated polymers traveling in a flow. There is also a need for more accurate methods for determining the length of single elongated polymers and/or distances between landmarks on single elongated polymers.

Citation of a reference herein shall not be construed as indicating that such reference is prior art to the present invention.

SUMMARY OF THE INVENTION

The present invention relates to methods and apparatus for the characterization of single polymers. In particular, the invention relates to methods and apparatus for determination of the velocities of single elongated polymers as they are caused to move relative to detection stations. The invention also relates to methods and apparatus for determining the length and molecular mass of single polymers, as well as to methods and apparatus for determining the distance between landmarks present on such polymers.

Broadly, the velocity of an elongated polymer, such as a DNA molecule having at least one detectable label, can be determined by a method in which the molecule is moved relative to at least two linearly sequential detection zones that are spaced apart a predetermined distance. As the label moves relative to a detection zone, it interacts with the zone to produce a signal amplitude profile. Each such profile is characterized in that it includes a leading edge in which the signal is increasing during a first time interval, a detection amplitude in which the signal remains substantially constant during a second time interal, and a trailing edge in which the signal is decreasing during a third time interval. A representation of the signal amplitude over the course of the first, second and third time intervals defines the signal amplitude profile. Each of the signal amplitude profiles is measured in a time-correlated manner, and then the time-correlated measurements can be analyzed to determine the velocity of the polymer.

Thus, in one embodiment, the signal amplitude profile from an individual label is determined at two linearly sequential detection zones that are spaced apart a predetermined distance. By measuring the time difference for a selected element of the signal amplitude profile to be detected at a first detection zone and at a second detection zone, and by dividing the predetermined distance between the zones by the measured time, the velocity of the polymer is determined. The selected element of the signal amplitude profile may be the center-of-mass of the profile, the temporal center of the profile, or some point, i.e., the half-way point, during the signal increase as the leading edge of the profile is detected or the signal decrease as the trailing edge of the profile is detected. It should be noted that the label need not be limited to a particular location. By comparing the signal amplitude profile characteristics at two different detection zones, the label can be such that it is detected for only a brief time, as for example, a single labeled polymeric base is detected, or it may be detected for a longer period of time, as for example, a polymer labeled with an intercalating dye travels entirely through two detection zones.

In a second embodiment of the present invention, the length of the polymer can be determined. In this embodiment, along with detecting an individual label on the polymer at two detection zones, the polymer must be detectable whenever any portion of it is positioned relative to a detection zone. Thus, for example, the polymer may be labeled with an intercalating dye that is detectable along the entire length of the polymer molecule. As the molecule moves relative to the detectors, the time difference between the detection of a selected element of the signal amplitude profile at the first detection zone and at a second detection zone is measured, and by dividing the predetermined distance between the zones by the measured time, the velocity of the polymer is determined. This value is then multiplied by the total time during which the polymer is detected at either of the detection zones, and the resulting product is the length of the molecule.

In a third embodiment of the present invention, the length between two detectable landmarks on the polymer can be determined. In this embodiment, two detectable landmarks are positioned on the polymer, and then the polymer is moved relative to two linearly sequential detection zones that are spaced apart by a predetermined distance. The polymer can be labeled with an intercalating dye or the like along its entire length, however, this is optional. The velocity of the polymer is determined using the methods described in the first embodiment above (using signal amplitude profiles obtained from either one of the landmarks or the optional intercalating dye), and the time difference between detection of one of the landmarks at a first detector and detection of that same landmark at a second detector is measured. When the calculated velocity is multiplied by the measured time difference between landmark detection, the resulting product is the distance between the landmarks.

BRIEF DESCRIPTION OF DRAWINGS

FIG. 8 is a schematic illustration of a third embodiment of an apparatus for formation of laser spots at multiple detection zones.

FIG. 9 is a schematic illustration of one embodiment of an apparatus to generate interference fringes.

FIG. 9A is a schematic representation of the fringe pattern within the spot of FIG. 9 as seen along line 9A—9A of FIG. 9.

DETAILED DESCRIPTION OF THE INVENTION

Figure 1:
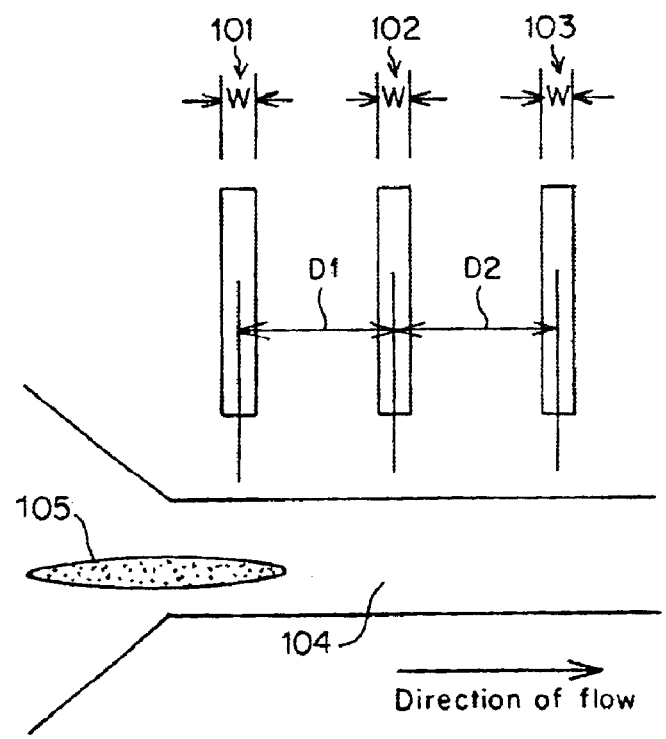
FIG. 1 is a schematic representation of the apparatus of the invention.
Figure 2:
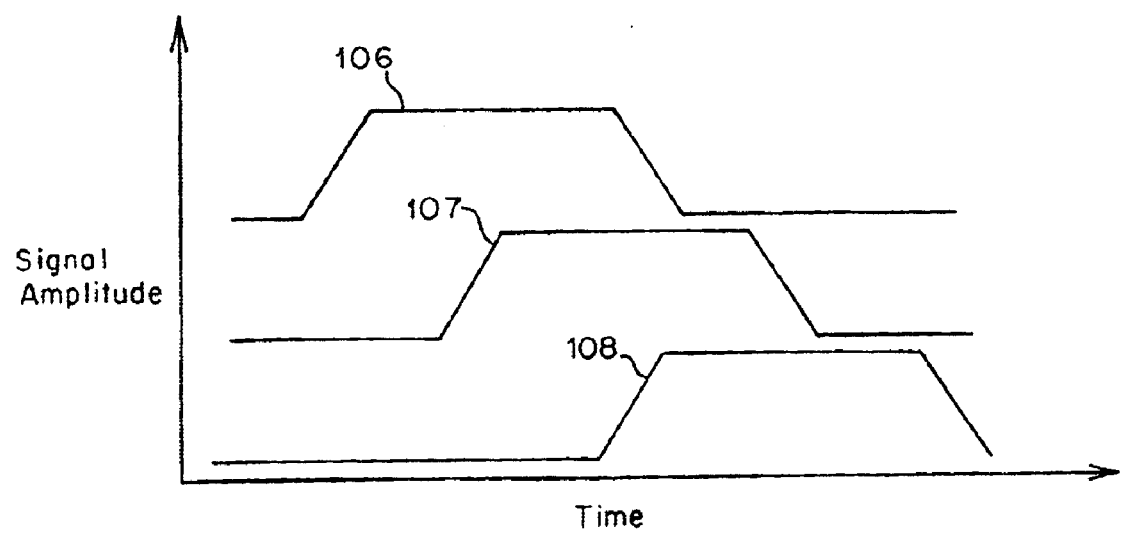
FIG. 2 is a schematic representation of several signal amplitude profiles measured using the apparatus of FIG. 1.

The present invention provides methods and apparatus for determining the velocities of single elongated polymeric macromolecules. The methods of the invention are based on time-correlated measurements of an elongated polymeric macromolecule at each of a plurality of detection zones. The detection zones are located along the travel path of the polymer at predetermined spacings. Signal amplitude profiles, e.g., intensity-time curves when fluorescence-based measurements are used, of an elongated polymeric macromolecule, are measured as the macromolecule passes through each of the detection zones. The measurements in the plurality of detection zones are time-correlated, e.g., synchronized, so that the temporal spacings between signal amplitude profiles measured at different detections zones are also determined. A schematic illustration of the invention is presented in FIG. 1. This apparatus is used to generate signal amplitude profiles as shown in FIG. 2. In FIG. 2, the signal amplitude profiles are positive, however, it should be apparent to one skilled in the art that negative signal amplitude profiles are also encompassed. For example, when absorption-based measurements are used, the signal amplitude will decrease when the polymer is in the detection zone.

As used herein, the term "elongated polymeric macromolecule" or "stretched polymeric macromolecule" refers to a polymer that is in a conformation in which the length of the molecule is substantially greater than its radius of gyration in the same solvent. Preferably the elongated polymeric macromolecule has a length which is substantially close to its contour length. An elongated polymer may be passed through an elongated channel. An "elongated channel" or "elongation channel" is a channel or pore through which a polymer can traverse. The channel, in some embodiments, has an opening which is only slightly larger than the cross-section of the elongated polymer.

As used herein, a "detection zone" refers to a region or volume which experiences movement relative to the polymeric macromolecule. Generally, the detection zones are fixed along a traveling path of a macromolecule, however, the invention contemplates a fixed macromolecule and traveling detection zones. The detection zone acts as a region in which a signal from the macromolecule is measured if the macromolecule, or a portion thereof, is present in the region or volume. In embodiments based on measuring laser induced fluorescence, a detection zone is defined by the excitation volume of a laser beam and the signal is the total fluorescence intensity emitted by the macromolecule or a portion thereof as it passes through the excitation volume.

As used herein, "time-correlated measurements" refers to measurements performed in different detection zones in such a manner that the temporal spacings between measured signals in different detections zones are known. Such time-correlated detection can be achieved by synchronizing measurements in all detection zones in real time. Alternatively, measurements in different detection zones may be time-correlated by a fixed, known time delay of detection in different detection zones. Methods for synchronized and time-delayed detection in different detection zones are well known in art and will be apparent to one skilled in art.

As used herein, a "signal amplitude profile" refers to the temporal profile of a measured signal. Each such profile is characterized in that it includes a leading edge in which the signal is increasing during a first time interval, a detection amplitude in which the signal remains substantially constant during a second time interal, and a trailing edge in which the signal is decreasing during a third time interval. A representation of the signal amplitude over the course of the first, second and third time intervals defines the signal amplitude profile. In embodiments involving optical detection, e.g., when macromolecules are detected by fluorescence, the signal amplitude profile is represented by the intensity versus time curve measured by a photodetector. Preferably, contributions to a signal amplitude profile due to the finite size of a detection zone are eliminated. In embodiments involving laser excitation, the laser beam profile is preferably deconvoluted from a measured intensity-time curve. Methods for eliminating the contribution of the finite size of a detection zone to a signal amplitude profile, e.g., a laser beam profile, are well known in art and can be performed by one skilled in the art.

The present invention also provides methods and structures that allow polymers of any length, including nucleic acids containing entire genomes, to undergo measurement of their velocities and lengths.

In carrying out the method of the invention, polymers are loaded into a device and run through channelled structures, propelled by forces which may include, but not be limited to kinetic, electrical or chemical forces. Stretching or elongation of the polymer can be achieved using any of the methods described in co-pending application U.S. Ser. No. 09/636,793, the teachings of which have been previously incorporated by reference. The stretching forces on the polymer are such that, in the case of an elongated DNA molecule, the molecule may be stretched to lengths much longer than the dimension of the detection zone. Since multiple molecules may be stretched in succession, extremely high throughput screening, e.g., screening of more than one molecule per second, can be achieved.

In the invention, single extended, labeled polymers are moved past detection zones. At such zones, labeled units of the polymers interact with the detector to produce a signal. As used in this application, "moved past" refers to embodiments in which the detection zones are stationary and the extended polymers are in motion, as well as to embodiments in which the detection zones are in motion and the extended polymers are stationary. Embodiments in which the detection zones and extended polymers are both in motion are contemplated as well.

Although the invention may be used for characterizing any polymer, it is preferable that the polymers have a predominantly, though not necessarily exclusively, linear or single-chain arrangement. Examples of such polymers include biological polymers such as deoxyribonucleic acids, ribonucleic acids, polypeptides, and oligosaccharides. The polymers may be heterogeneous in backbone composition, thereby containing any possible combination of individual monomer units linked together, e.g., peptide-nucleic acids (PNA), which have amino acids linked to nucleic acids. In a preferred embodiment, the polymers are homogeneous in backbone composition and are, e.g., nucleic acids, polypeptides or oligosaccharides. The term "backbone" is given its usual meaning in the field of polymer chemistry. A nucleic acid as used herein is a biopolymer comprised of nucleotides, such as deoxyribose nucleic acid (DNA) or ribose nucleic acid (RNA). A protein or polypeptide as used herein is a biopolymer comprised of amino acids. In the most preferred embodiment, the extended object is a double-stranded DNA molecule.

A polymer is made up of a plurality of individual units, i.e., monomeric units or monomers, which are building blocks that are linked either directly or indirectly to other building blocks or monomers to form the polymer. The polymer preferably comprises at least two chemically distinct linked monomers. The at least two chemically distinct linked monomers may produce or be labeled to produce different signals. Different types of polymers are composed of different monomers. For example, DNA is a biopolymer comprising a deoxyribose phosphate backbone to which are attached purines and pyrimidines such as adenine, cytosine, guanine, thymine, 5-methylcytosine, 2-aminopurine, hypoxantine, and other naturally and non-naturally occurring nucleobases, substituted and unsubstituted aromatic moieties. RNA is a biopolymer comprising a ribose phosphate backbone to which are attached purines and pyrimidines such as those described for DNA but wherein uracil is substituted for thymidine. Deoxyribonucleotides may be joined to one another via an ester linkage through the 5' or 3' hydroxyl groups to form the DNA polymer. Ribonucleotides may be joined to one another via an ester linkage through the 5', 3' or 2' hydroxyl groups. Alternatively, DNA or RNA units having a 5', 3' or 2' amino group may be joined via an amide linkage to other units of the polymer.

The polymers may be naturally-occurring or non-naturally occurring polymers. Polymers can be isolated, e.g., from natural sources using biochemical purification techniques. Alternatively, polymers may be synthesized, e.g., enzymatically by in vitro amplification using the polymerase chain reaction (PCR), by chemical synthesis, or by recombinant techniques.

The structures of the invention are used in conjunction with methods for analyzing the extended polymers by detecting a physical quantity which transmits or conveys information about the structural characteristics of an extended polymer. A physical quantity, as used herein, can either be a measurable intrinsic property of a particular type associated with one or more monomers of an extended polymer, e.g., the distinct absorption maxima of the naturally occurring nucleobases of DNA (referred to herein as intrinsic labeling), or a measurable property of a compound that is specifically associated with one or more monomers of an extended polymer (referred to herein as extrinsic labeling). Preferably the physical quantity is proportional to the number of monomers in the detection zone. An extrinsically labeled polymer may be labeled with a particular fluorescent dye with which all nucleobases of a particular type, e.g., all thymine nucleobases, in a DNA strand are labeled. Alternatively, an extrinsically labeled polymer may be a fluorescently labeled oligonucleotide of defined length and sequence that hybridizes to and therefore "marks" the complementary sequence present in a target DNA. An extrinsic label of this sort is referred to as landmark or a unit specific marker. Thus, a landmark is an extrinsic label that identifies a specific sequence within the polymer that is more than one unit in length. Molecules, or markers, that can be used to labeled polymers may further include, but are not limited to, sequence specific major or minor groove binders and intercalators, sequence-specific DNA or peptide binding proteins, sequence specific PNAs, etc. The detectable physical quantity may be in any form that is capable of being measured. For instance, the detectable physical quantity may be electromagnetic radiation, electrical conductance, heat conductance, radioactivity, etc. The measured signal may arise from energy transfer, directed excitation, quenching, changes in conductance (resistance), or any other physical changes. In one embodiment, the measured signal arises from fluorescence resonance energy transfer ("FRET") between the marker and the station, or the environment surrounding the station. In preferred embodiments, the measured signal results from direct excitation in a confined or localized region, or epiillumination of a confocal volume or a slit-based excitation. Possible analyses of polymers include, but are not limited to: determination of polymer length, determination of polymer sequence, determination of polymer velocity, determination of the degree of identity of two polymers, determination of characteristic patterns of unit-specific markers of a polymer to produce a "fingerprint", and characterization of a heterogeneous population of polymers using a statistical distribution of unit-specific markers within a sample population. The exemplary labels include but are not limited to intercalator dyes: YOYO-1, TOTO-1, YOYO-3, TOTO-3, POPO-1, POPO-3, JOJO-1, JOJO-3, BOBO-1, BOBO-3 (from molecular probes); non-intercalator/backbone staining dyes (these dyes chemically attach to the backbone of DNA): Panvera-fluorescein kit, Panvera-Cy3 kit, Panvera-Cy 5 kit; fluorescent probe dyes: fluorescein, tetramethylrhodamine, Alexa dyes, Oregon dyes, Cy dyes, IR dyes; and other types of labels, e.g., latex spheres, gold particles, and streptavidin-biotin conjugates.

There are numerous methods and products available for analyzing polymers as described in PCT Publication No. WO 98/35012, which is incorporated herein by reference in its entirety.

Various methods for analyzing polymers differ in their potential sensitivity and resolution, e.g., the minimum distance between two detection zones. A low resolution technique is capable of measurements in two detection zones having a large distance between them; a high resolution technique is capable of measurements in two detection zones having a smaller distance between them. The resolution of a particular technique is determined by the characteristic distance through which the detection method may sense the particular physical quantity of an extended polymer. For example, the resolution of optical methods is dictated by the diffraction limit.

In the following, for simplicity reasons, optical detection methods are often used. It will be apparent to one skilled in the art that other detection methods can be used in conjunction or in place of optical detections.

Velocities of Single Elongated Polymers

The methods of the invention are based on time-correlated measurements of elongated polymers as they travel past two or more detection zones which are spaced apart by known, pre-determined distances. A schematic illustration of one embodiment of the apparatus of the invention is presented in FIG. 1. For example, detection zones 101 and 102 are separated by a distance represented as D1. The corresponding time-correlated signal amplitude profiles 106 and 107 shown in FIG. 2 are temporally separated by the time the polymer (105) takes to travel the distance D1 between the detection zones. As the polymer passes each detection zone, a signal amplitude profile is generated. These are depicted schematically in FIG. 2, in which the polymer 105 first passes detection zone 101 which generates profile 106, then passes detection zone 102 which generates profile 107, and finally passes detection zone 103 which generates profile 108. Signal amplitude profiles are then used to determine the velocity of the polymer. Of course, the invention is not intended to be limited to the use of three detection zones. Rather, as few as two detection zones may be employed, while the maximum number of such zones is virtually unlimited.

Figure 3:
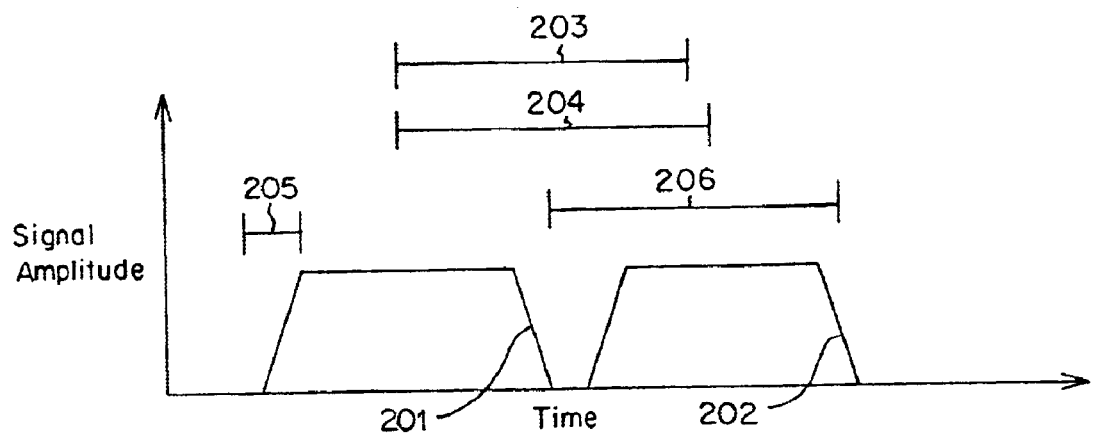
FIG. 3 is a schematic illustration of several time-correlated signal amplitude profiles.
Figure 4:
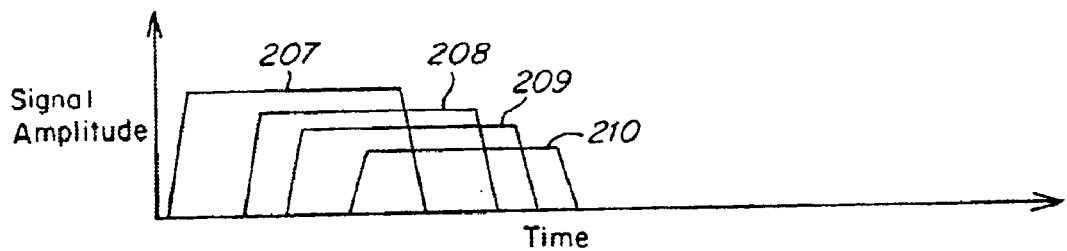
FIG. 4 is a schematic illustration of several time-correlated signal amplitude profiles measured at multiple detection zones.
Figure 5:
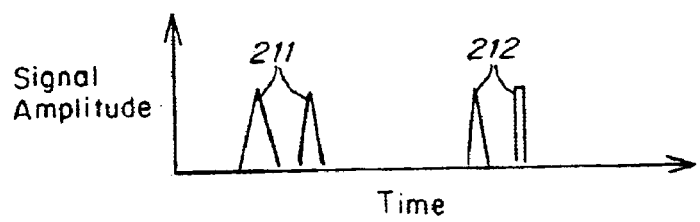
FIG. 5 is a schematic illustration of signals detected at first and second detection zones.

As will be described in greater detail below, FIGS. 3, 4 and 5 illustrate various ways different types of velocity can be determined from measured signal amplitude profiles. The distance between each pair of detection zones can be selected based on the expected test conditions and/or requirements of the measurements. For example, when a steady flow is involved such that the polymer velocity of polymers is not expected to vary over a range of distances, larger distance between the detection zones may be used. Alternatively, when flow changes rapidly and/or the polymers vary in length rapidly, multiple closely spaced detection zones are preferred (as shown in FIG. 4). In a preferred embodiment, the distances between the detectors are less than the length of an elongated polymer. Shorter distances between the detectors tend to cause the average measured velocity to be closer to the actual measured velocity at both detectors. Thus in some preferred embodiments, the distances between detectors approach the minimum allowed by the resolution of the detection zones and their detection methods. For example, in methods based on optical measurement, the distances between detection zones are at or close to the diffraction limit.

Distances among detection zones can be determined using any methods known in the art. In one embodiment, the distances are measured by mechanical systems that offer high spatial resolution. In another embodiment, the distances can be measured by calibration using elongated polymers of a known length. In still another embodiment, the distances can be measured by calibration using a fluid flow of known velocity. Such calibration methods are well known in the art.

Due to its flexibility, the conformation of a polymer may be constantly changing. As a consequence, each point on the polymer may have a different velocity from another point on the polymer. For polymers in a fluid flow, the velocity of an elongated polymer is also affected by the fluid flow 104. The velocity of a single elongated polymer can be described in various manners.

In FIG. 3, various velocity measurements are represented for first 201 and second 202 signal amplitude profiles measured at first and second detection zones. Various time intervals, used for the velocity determination, are depicted in FIG. 3 as well.

The velocity of an elongated polymer can be represented by the velocity of its center-of-mass (COM). In one embodiment, the COM can be found by obtaining the signal amplitude profile as the molecule moves past each detector, and then calculating the time at which half of the sum of the signal intensities has occurred. The COM velocity can be measured by determining the time interval the center-of-mass of the elongated polymer requires to travel between two detection zones separated by a known distance. This time interval is represented by the bar labeled reference numeral 204 in FIG. 3. The COM velocity is especially useful when the molecule elongates or shortens during passage through the system. For example, the COM velocity based on measurements of intercalator signal takes into account any variations in stretching because varying regions of stretching will have proportionately higher or lower intensity of the intercalator signal.

The velocity of an elongated polymer can also be represented by the velocity of its contour center, i.e., the midpoint of its molecular contour (center-to-center velocity). The center-to-center velocity can be measured by determining the time interval the contour center of an elongated polymer requires to travel between two detection zones separated by a known distance. This time interval is represented by the bar labeled reference numeral 203 in FIG. 3. Depending on whether the polymer is uniformly elongated or not, the center-to-center velocity can be the same or different from the COM velocity. In particular, if the polymer is not uniformly elongated, the center-to-center velocity is generally different from the COM velocity.

The velocity of an elongated polymer can also be represented by the velocity of its leading or trailing end, i.e., end-to-end velocity. The end-to-end velocity can be measured by determining the time interval the leading or trailing end of an elongated polymer requires to travel between two detection zones separated by a known distance. This time interval is represented by the bar labeled reference numeral 206 in FIG. 3.

The velocity of an elongated polymer can also be represented by the rise-time velocity which is defined as the velocity of the leading end of the elongated polymer traverse through a region of finite size. A rise-time velocity can therefore be measured by dividing the size of the region with the time required for the leading end of the polymer to travel from the entry edge of the region to the exit edge of the region. This time interval is represented by the bar labeled reference numeral 205 in FIG. 3. Rise-time velocity is particularly useful when the leading end of the polymer is labeled.

Any single type of velocity can be used either independently or in combination with one or more other types of velocity for the characterization of an elongated polymer. The measured velocity can be used to determine the polymer length and/or distances between markers on an elongated polymer.

The methods of detection can be based on optical methods, including but not limited, to light induced fluorescence measurements, absorption measurements, light scattering measurements and non-linear optical measurements. Such optical methods are well known in the art. For example, when light induced fluorescence measurements or absorption measurements are to be used, those of ordinary skill in the art will know how to choose, the excitation source, the wavelength, the detector, and so on.

In some embodiments, the signal measured at the detection zone is the light induced fluorescence of an elongated polymer. In one embodiment, laser induced fluorescence of monomers in the polymer is measured. In another embodiment, laser induced fluorescence of intercalating dye molecules is measured. In still another embodiment, light induced fluorescence from fluorescent markers labeled at discrete locations along the polymer, e.g., at the leading or trailing ends, is measured. In other embodiments, a slit of selected width is used to define the detection zone. In this embodiment, the excitation can be selected from the emitted wavelengths of a lamp and the detection zone is illuminated through the slit. When a slit is used, it is preferred that the slit be of a width that is close to the diffraction limit of the wavelength of light used so that the highest resolution can be achieved.

In other embodiments, the signal measured at the detection zone can be based upon the absorption of an elongated polymer. In such embodiments, the measured wavelength or wavelengths of the absorbed light are proportional to the number of monomers falling within the detection region. In one embodiment, laser excitation is used in the absorption measurements. In this embodiment, a laser beam of a selected wavelength is used to define the detection zone. In another embodiment, a slit of select width is used to define the detection zone. As such, the excitation can be selected from the emitted wavelengths of a lamp and the detection zone is illuminated through the slit.

The signal measured at the detection zone can also be light scattered by a polymer labeled with molecules having light-scattering properties. As noted above, a laser beam of a selected wavelength can be used to define the detection zone or, alternately, a slit of select width is used to define the detection zone.

Figure 6:
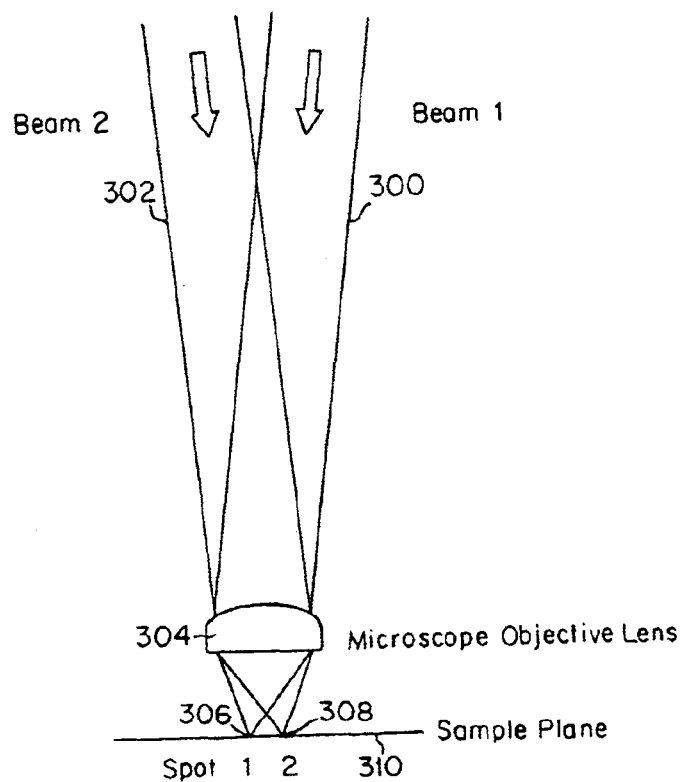
FIG. 6 is a schematic illustration of one embodiment of an apparatus for formation of laser spots at multiple detection zones.

Various methods can be used to define multiple detection zones in the present invention. In methods based on optical measurements, detection zones can be generated using laser illumination spots. In embodiments which employ multiple lasers, a separate laser can be used to generate each spot. In that embodiment, the lasers are arranged such that the collimated output of the lasers converges on the output aperture of a microscope objective. As such, each beam is caused to enter the microscope objective at a different angle. The angular displacement of the beams is converted by the objective lens to a spatial separation of the focused laser spots as shown schematically in FIG. 6. Specifically, in FIG. 5, two separate laser beams 300, 302 pass through a microscope objective lens 304 which resolves them into two separate spots 306, 308 on a sample plane 310. The spatial separation of the spots can be controlled by adjusting the angular separation of the beams. The larger the angular separation, the larger the spatial separation.

Figure 7:
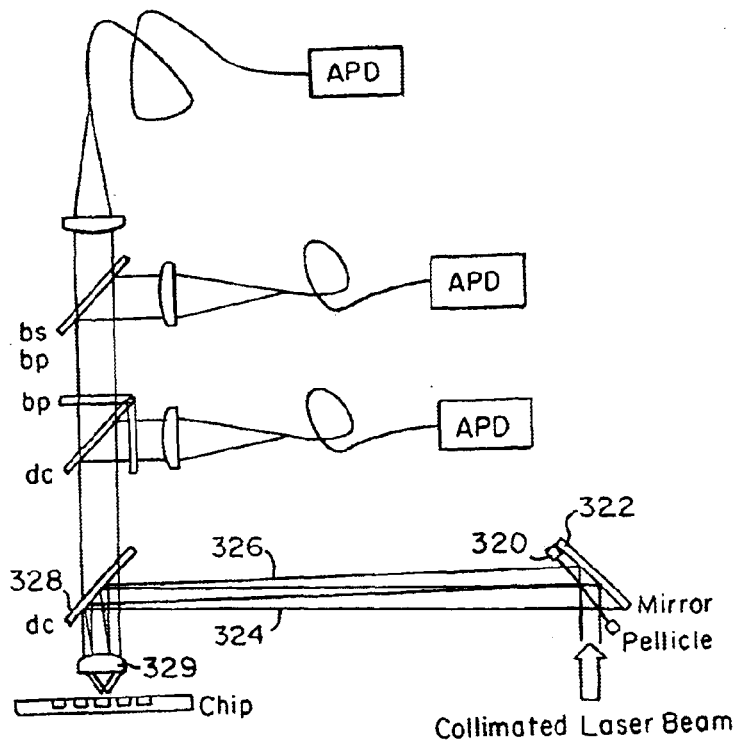
FIG. 7 is a schematic illustration of a second embodiment of an apparatus for formation of laser spots at multiple detection zones.

In other embodiments, multiple detection zones can be defined by splitting the output of a single laser to create angularly displaced beams. In one embodiment depicted schematically in FIG. 7, a first partially reflecting beamsplitter 320 and a fully reflective mirror 322 can be employed to create two beams 324, 326 that converge on a second partially reflecting beamsplitter 328 which reflects the beams onto the output aperture of a microscope objective 329. The angular separation is controlled by setting the spacing and angles between the first partially reflecting beamsplitter 320 and the fully reflecting mirror 322. In a preferred embodiment, the partially reflecting beamsplitter is a pellicle type of beamsplitter. The very thin membrane of the pellicle means that a ghost beam from the rear surface of the beamsplitter is effectively avoided.

In still another embodiment, such as that shown schematically in FIG. 8, a diffractive optical element such as a phase grating is used to split a monochromatic laser beam into multiple beams at various grating orders, e.g., a zero order (straight through) beam, first order beams and higher order beams. The distribution of energy into the different orders is determined by the depth of grooves formed in the phase grating, whereas the angular separation of different orders of beams is determined by groove spacing. In this embodiment a collimated laser bean is bent by a fully reflective mirror 330 and passed through a phase grating 332. A second optical element, such as a lens 334, is used to collect the diverging beams from a diffractive optics and refocus the beams 336, 338, so that they converge and encounter a partially reflecting beamsplitter 340 and are reflected toward a microscope objective 342.

In yet another embodiment, shown schematically in FIGS. 9 and 9A, a fringe pattern of alternating dark and bright bands formed within a single illumination spot 350 is used to define detection zones. An elongated polymer, such as a DNA molecule, moves through the spatially periodic bands. In one preferred embodiment, an elongated polymer is labeled with one or more fluorescent labels. As the elongated polymer moves through the bands, any bound fluorescent labels will emit fluorescence in proportion to the illuminating light. The movement of the fluorescent labels will therefore result in a temporally periodic emission. The time pattern of emission can be measured, and by knowing the spatial periodicity, i.e., the fringe spacing, the velocity of the DNA can be calculated from the measured temporal periodicity. In a related embodiment, the backbone of an elongated DNA molecule is stained with a fluorescence dye. In this embodiment, a stairstep pattern of emission will be observed as successively more of the bright bands illuminate DNA. While not intending to be limited as such, the fringe pattern can be created by overlapping, in a single illumination spot, two beams 352, 354 that have been formed from a single laser and passing those beams through a microscope objective lens 356, as represented schematically in FIG. 9. The resulting fringe spacing is one half the wavelength of the illuminating light when the two beams are oriented 180 degrees to each other. At other angles, the fringe spacing is larger and can be found from D=/2sin(q), where D is the fringe spacing, is the wavelength of the illuminating laser and q is the half-angle between the two laser beams. The illumination spot preferably is a few microns in size such that a sufficient number of fringes are formed.

The optical methods described above can also be combined. For example, elongated DNA molecules labeled with both intercalating dye and sequence specific fluorescence markers are contemplated. Preferably, the intercalating dye and the fluorescence markers emit light of different and distinguishable wavelengths. In such an embodiment, signal amplitude profiles 201, 202, 211, 212 illustrated by both FIG. 3 and FIG. 5 are simultaneously determined for a DNA molecule. Any dual color configurations for measuring fluorescence from both the intercalating dye and the fluorescence markers can be used. Such configurations are described, for example, in Deniz et al., 1999, Proc. Natl. Acad. Sci. USA. 96:3670–3675; and Ha et al., 1996, Proc. Natl. Acad. Sci. USA. 93:6264–6268.

Any methods known in the art for elongating single macromolecule polymers, such as single DNA molecules, can be used in the invention. These include the methods described in the previously incorporated co-pending application U.S. Ser. No. 09/636,793. Single elongated polymers are then delivered to the detection region of the apparatus which is preferably located along the path of the elongated molecule to allow measurements of molecular properties of the molecule to be performed.

Center-of-Mass Velocity of Polymers

Various methods can be used to determine the COM velocity of an elongated polymer. Any detection methods that allow measuring the mass of the section of an elongated polymer falling within a detection zone can be used. Such detection methods can be, but are not limited to, optical detection methods and electrical detection methods.

In a preferred embodiment, the COM velocity is determined from measured intensity-time curves of a DNA molecule stained with intercalating dye molecules. It is well known in the art that the amount of intercalating dye molecules bound to a DNA molecule is proportional to the length of the DNA molecule. For example, intercalating dye YOYO-1 binds to DNA molecules at a dye:base pairs ratio of 1:5 (see, e.g., Larsson et al., 1994, J. Amer. Chem. Soc. 116:8459–8465). The fluorescence intensity of the intercalating dye is therefore proportional to the length or mass of the DNA molecule. Thus, the center-of-mass of a DNA molecule can be determined from the measured fluorescence intensity-time curve by integrating the fluorescence intensity as a function of time according to the equation:

$$L_{com} = \frac{\int_{t_1}^{t_2} I(t) \cdot L(t) \, dt}{\int_{t_1}^{t_2} I(t) \, dt} \quad (1)$$

Where $L_{com}$ is the location of the center-of-mass along the polymer, $I(t)$ is the fluorescence intensity measured at time t, $t_1$ and $t_2$ designate the time when the polymer enters and leaves $$L(t) = \int_{t_1}^{t} v(\tau) \, d\tau$$

the detection zone, respectively, and $L(t)$ is the length of the polymer that has passed through the detection zone at time t. Any time before $t_1$ can be used as the lower bound of the integral and any time after the time $t_2$ can be used as the upper bound of the integral. $L(t)$ can be determined according to equation (2)

$$(2)$$

where $v(t)$ is the velocity of the polymer at time t. Thus the temporal location of the center-of-mass $t_{com}$ of an elongated polymer can be determined by solving the equation $$\int_{t_1}^{t_{com}} v(t) \, dt = \frac{\int_{t_1}^{t_2} I(t) \cdot \left[ \int_{t_1}^{t} v(\tau) \, d\tau \right] dt}{\int_{t_1}^{t_2} I(t) \, dt} \quad (3)$$

In cases where the velocity of the polymer is constant, i.e., $v(t)=V$, the temporal location of the center-of-mass can be determined by the equation $$T_{com} = \frac{\int_{t_1}^{t_2} I(t) \cdot t \, dt}{\int_{t_1}^{t_2} I(t) \, dt} \quad (4)$$

The COM velocity is then determined by dividing the distance between two detection zones of known distance with the difference in $T_{com}$ at the two detection zones.

In another embodiment, the COM velocity is determined from the measured intensity-time curve of intrinsic stimulated fluorescence from an elongated polymer. When monomer units of a polymer can be excited by light and fluoresce at a detectable wavelength, intensity-time curves can be measured by monitoring fluorescence at the emitted wavelength. When this approach is to be used, it is preferable that the fluorescent monomers are evenly distributed along the polymer. The fluorescence intensity then provides a measure of the length or mass of the polymer.

Center-to-Center Velocity of Polymers

Depending on the channel geometry used for delivering the polymers, a center-to-center approximation of the velocity of the polymer can be used. For example, a center-to-center velocity of an elongated DNA can be used where a constant flow profile is generated. The center-to-center velocity is generally different from the center-of-mass velocity. The center-to-center velocity is determined by measuring the time interval for the mid point of the molecular contour of an elongated polymer, i.e., the center of the polymer contour, to travel between two detection zones separated by a known distance. The center of an elongated polymer is defined as $$L(t_c) = \frac{L(t_1) + L(t_2)}{2} \quad (5)$$

where $L(tc)$, $L(t_1)$ and $L(t_2)$ are defined by Eq. (2). In cases where the velocity of the polymer is constant, i.e., $v(t)=V$, the temporal location of the center of the polymer can be determined by the equation $$t_c = \frac{t_1 + t_2}{2} \quad (6)$$

where $t_c$ is the temporal location of the center of the measured signal amplitude profile, e.g., intensity-time curve, of the polymer, and $t_1$ and $t_2$ are the leading and trailing edges of the signal amplitude profile, respectively. The center-to-center velocity is then determined by dividing the distance between two detection zones with the difference in $t_c$ at the two detection zones.

In some cases, e.g., when a polymer is elongated such that its mass is uniformly distributed across its length, the center-to-center velocity is the same as the center-of-mass velocity.

End-to-End Velocity of Polymers

The end-to-end velocity is determined using the entrance or exit of the elongated molecule through two detection zones. In some embodiments, a leading edge to leading edge velocity is determined by measuring the leading edge of the polymer passing through the two detection zones. In other embodiments, a trailing edge to trailing edge velocity is determined by measuring the trailing edge of the polymer passing through the two detection zones. End-to-end velocity can be measured by any methods that are capable of detecting the ends of a polymer.

In some embodiments of the invention, the end-to-end velocity of an elongated polymer is determined from signal amplitude profiles measured at two detection zones by a method that allows measuring the mass of polymer a section in each detection zone. In a preferred embodiment, the polymer is a DNA molecule labeled along its entire length with an intercalating dye. The entrance of the DNA molecule into a detection zone is marked by an increase in the intercalator signal. The exit of the DNA molecule from the detection zone is marked by a decrease in the intercalator signal. Using the known distance of separation in the detection zones, the velocity can be determined using any combination of edges of the intensity-time curves and their respective times of entry/exit into their respective detection zones. In one embodiment, a time of entry or exit of the polymer in the detection zone is identified as the temporal location where intensity-time curve begins to deviate from the background level. In another embodiment, a time of entry or exit of the polymer is identified as the time at the half height of the leading or trailing edge of the intensity-time curve. The end-to-end velocity is then determined by dividing the distance between two detection zones with the difference in the entry or exit times at the two detection zones.

In other embodiments, the polymer is labeled at one or both ends and the label is detected to determine the end-to-end velocity. For example, the polymer can be labeled at one end with a fluorescent dye molecule. The fluorescence signals are detected at two detection zones separated by a known distance. The end-to-end velocity is determined by dividing the distance between the two detection zones by the measured time interval between the signals. Because the polymer can enter the detection zones with either its labeled end or its unlabeled end as the leading edge, it is important that the polymer travel from the first detection zone to the second detection zone without switching leading and trailing ends. This condition is normally satisfied if no obstacles are located between the two detection zones.

In a preferred embodiment, the polymer is labeled at both ends with the same dye. Two fluorescence signals are detected at each detection zone. The end-to-end velocity can be determined by the two first signals or the two second signals. Labeling of the polymer at both ends is more preferred than labeling of the polymers at one end, since the detection of two correlated signals corresponding to the labels at the leading and the trailing edges at each detection zone can be used to confirm the detection of the labeled ends of a polymer. This is especially important when loose dye molecules or other fluorescent specifies may be present in the sample. In another preferred embodiment, the two ends of a polymer can be labeled with dyes having different emission spectra.

Velocity of Polymers from Rise-Time Measurements

The rise-time approximation allows the determination of the velocity of an elongated polymer by dividing the time required for the leading edge of the polymer to traverse the detection zone into the known length of the detection zone. Alternately, the velocity of an elongated polymer can be determined by dividing the time required for the trailing edge of the polymer to traverse the detection zone into the known length of the detection zone. In contrast to COM, center-to-center and end-to-end velocities, the rise-time velocity is determined using only one detection zone.

In some embodiments of the invention, the rise-time velocity of an elongated polymer is determined from signal amplitude profiles measured at a detection zone by a method that allows measuring the mass of polymer section in the detection zone. In a preferred embodiment, the polymer is a DNA molecule labeled with intercalating dye. The entrance of the DNA molecule into a detection zone is marked by a rise in the intercalator signal. The exit of the DNA molecule from the detection zone is marked by a decrease in the intercalator signal. The intercalator signal from the DNA reaches full intensity as the front end of the DNA molecule reaches the far-edge of the detection zone. Thus, in an intensity-time curve, rise-time is represented by the leading edge of the intensity-time curve. The rise-time velocity is then determined by dividing the detection zone length by the time interval in which it takes the leading end of the signal amplitude profile to reach full intensity. In one embodiment, the detection zone is defined by the spot size of a laser excitation beam from a 532 nm diode pumped solid-state laser focused to a beam waist of about 266 nm. In that embodiment, the resolution of rise-time velocity is 266 nm divided by the rise-time.

Determination of the Velocity of Polymers Labeled with Markers at Known Distances on the Polymer The velocity of elongated polymers can also be determined by monitoring the time interval between markers on the polymers at known distances. In such embodiments, because the distance between two or more markers on a polymer is known, the velocity of the polymer can be determined using a single detection zone.

In a preferred embodiment, sequence specific markers are used to label the DNA molecule. Such markers can comprise, for example, fluorescently labeled oligonucleotides of defined sequences that hybridize to and therefore "mark" complementary sequences present on a target DNA molecule. The distance between each adjacent pair of markers is preferably greater than half the dimension of the detection zone so that signals from adjacent markers can be distinguished. The velocity of the polymer is then determined by dividing the known distance between a pair of markers with the time interval between detection of the signals from the two markers. Any sequence specific markers can be used in the present invention. These include, but are not limited to, fluorescently labeled sequence specific major or minor groove binders and intercalators, sequence-specific DNA or peptide binding proteins, sequence specific peptide nucleic acids (PNAs), and the like.

Two or more of the methods described above can be combined to give additional information about the motion of elongated polymers. In one embodiment, COM velocity and end-to-end velocity are determined and compared for an elongated polymer. A difference between COM velocity and end-to-end velocity indicates that the length of the polymer may have been changing as the polymer passed through the detection zones. In another embodiment, rise-time velocity can be used to estimate the size of the detection zone. The rise-time velocity is subtracted from a simultaneously determined COM velocity, center-to-center velocity and/or end-to-end velocity such that the contribution of the finite size of the detection zone is eliminated.

Determination of Polymer Lengths

The invention also provides methods for determining lengths of single elongated polymers and for determining distances between tags along single elongated polymers. The length of the polymer or the distance between two markers on a polymer, can be determined using discrete detection zones if the velocity of the polymer is known. For example, if the velocity of a polymer is v(t), then the length of the polymer can be determined from the signal amplitude profile measured at a detection zone according to the equation:

$$L = \int_{t_1}^{t_2} v(t) \, dt \tag{7}$$

where L is the length of the polymer, and $t_1$ and $t_2$ are the leading and trailing edges of the signal amplitude profile.

In some embodiments of the invention, the velocity of the polymer is approximated by a time independent velocity V.

In such embodiments, the length of the polymer can be determined as $L = V \cdot (t_1 - t_2)$.

However, since the velocity of the polymer may be changing upon passage through the region of interest, it is preferable to provide multiple detection zones along the path of the elongated polymer so that multiple signal amplitude profiles can be obtained. In one embodiment, the spacings between each adjacent pair of detection zones are much smaller than the length of the elongated polymer. In such an embodiment, overlapping signal amplitude profiles along the strand of the elongated polymer can be obtained, permitting determination of time dependent velocity v(t). This will increase the accuracy of the velocity measurements and allow a more accurate measurement of the polymer length. A schematic of the output is shown in the following FIG. 4. In FIG. 4, four signal amplitude profiles 207–210 of an elongated polymer are shown (with arbitrary relative intensities). Any of the different types of velocities can be used in the multiple detection scheme. For instance, velocity determination can further be estimated by using a combination of leading edge velocity information, center-of-mass estimations, rise time estimations, and other information that can be obtained from the intercalator signal.

Single-Molecule Restriction Mapping

The methods and apparatuses of the invention can be used in analysis of polymers, such as for example, single-molecule restriction fragment length polymorphism (RFLP). In one embodiment, a suitable restriction enzyme or enzymes are used to produce restriction fragments. Any restriction enzymes can be used in conjunction with the invention. The recognition sequences and reaction conditions of many restriction enzymes are well known to one skilled in the art. Depending on the sequences of the DNA molecules that are to be analyzed, suitable restriction enzymes can be selected. A sample containing fragments from restriction digestion is then labeled. For example, labeling may comprise staining the sample with an intercalating dye, such as YOYO-1. The labeled fragments are then elongated and detected by any method of the invention. Two or more detection zones are located in the region where the lengths of single restriction fragments are measured.

In another embodiment, modified restriction enzymes that recognize and bind to their recognition sequences but do not cleave the substrate DNA molecule can be used to label a DNA molecule. Alternately, a restriction enzyme can be used in conjunction with a buffer, such as a solution of low concentration Mg2++, such that the restriction enzymes recognize and bind to their recognition sequences but do not cleave the substrate DNA molecule. In each of these cases, the restriction enzymes are labeled using, for example, fluorescent labels. DNA molecules labeled in this manner are then elongated and distances between labels along the DNA molecules are measured. Of course, other sequence specific labels can be used in place of or in conjunction with labeled non-cleaving restriction enzymes. Such sequence specific labels include but are not limited to sequence specific major or minor groove binders and intercalators or sequence specific PNAs, and the like.

A combination of cleaving and non-cleaving restriction enzymes can also be used. In one embodiment, restriction enzymes that cleave a substrate can be used to generate restriction fragments. The resulting restriction fragments are stained with an appropriate intercalating dye. Non-cleaving restriction enzymes labeled with a fluorescence dye of a wavelength different and distinguishable from that of the intercalating dye are then used to label internal restriction sites in these restriction fragments. Simultaneous detection of both wavelengths allows determination of lengths of restriction fragments and identification of internal sequences. Other sequence specific labels can be used in place of or in conjunction with labeled non-cleaving restriction enzymes. As above, such sequence specific labels include but are not limited to sequence specific major or minor groove binders and intercalators or sequence specific PNAs, etc.

EXAMPLE

Stretching of Phage λ-DNA

Figure 10:
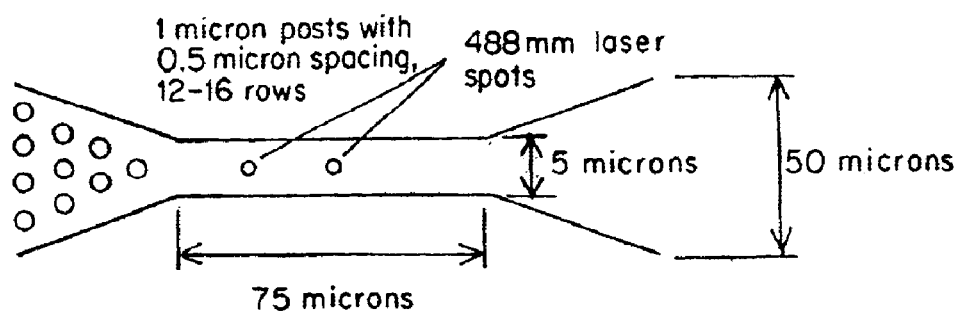
FIG. 10 is a schematic representation of the apparatus of the invention showing positioning of laser spots defining the detection zones.

FIGS. 11A–11C, 12 and 13 were derived using a dual laser spot arrangement as illustrated in FIG. 10. The DNA was driven through a quartz chip having an etched nanochannel of the following design: A nanochannel was formed in a 300 nm quartz chip using electron beam lithography. The process employed a series of lithographic steps known in the art, including a) coating the quartz wafer with a resist, b) exposing a pattern on the coated chip to an electron beam, c) stripping the exposed resist, d) etching using reactive ion etch to give straight wall profiles, and e) removing the remaining resist.

The detection zones were laser spots formed by an argon ion laser running at 488 nm and delivering about 2 mW of laser power to each of the spots. The spots were diffraction limited, with a spot size of approximately 0.5 microns in diameter. The laser spots were spaced 15 mm apart and located within the nanochannel in the path of the DNA molecules. A carrier liquid containing labeled DNA was flowed through the nanochannel in a manner such that laminar flow lines allowed the DNA to be delivered through the two laser spot detection zones. The DNA molecules comprised -DNA that was intercalated with YOYO-1 at a final concentration of one YOYO-1 molecule/10 base-pairs. The carrier solution contained 100 mM DTT in a 1× TBE solution. A fluid drive, delivering 50 psi, was used to drive the DNA through the channel. The chip was sealed using known chemical activation sealing techniques. The surfaces to be bonded (the quartz chip and a quartz coverslip) were activated using an ammonium hydroxide:peroxide:water mixture, heated to 70° C. The coverslip and the quartz chip were then pressed together under water and the clamped package was baked to evaporate any solvent and cause chemical bonding of the two surfaces. The DNA sample mixture was then introduced into the chip by capillary forces. The signals measured from the two laser excitation spots, arranged 15 mm apart, were collected through a Nikon 1.4 NA 100× oil immersion objective. The resultant fluorescent signals were filtered and detected by two avalanche photodiodes. The signals from the two intercalator signals were then collected through a data capture board, processed through an A/D converter, and stored on a computer. The computer allowed processing of the data and calculation of the lengths of the molecules. A constant velocity estimation was used to derive the velocity of the molecules moving through the system. The velocity was a COM to COM velocity estimation/calculation. The average length of the lambda molecules was measured to be around 18 microns, corresponding to an approximate 20% increase in the length of the DNA molecule from the intercalator staining. The data was processed using an algorithm written in MATLAB data processing language.

Figure 11A:
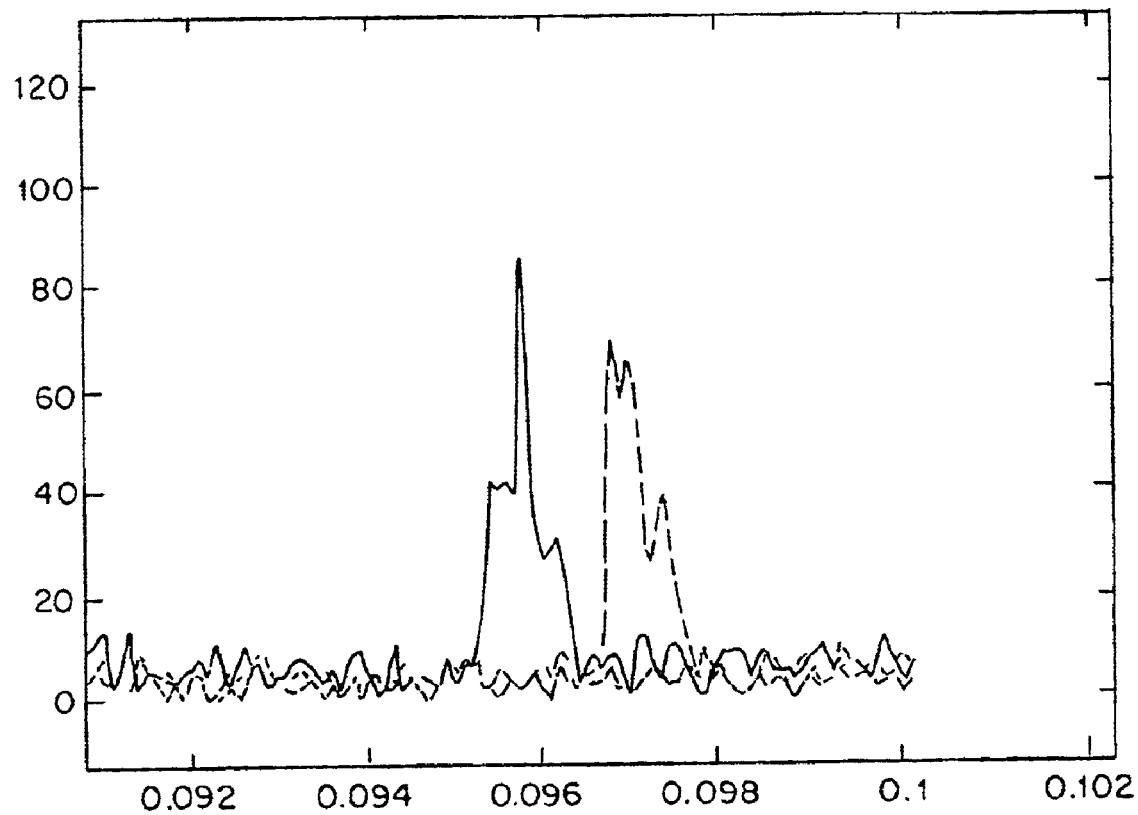
FIGS. 11A–11C show exemplary signal amplitude profiles measured at two detection zones.
Figure 11B:
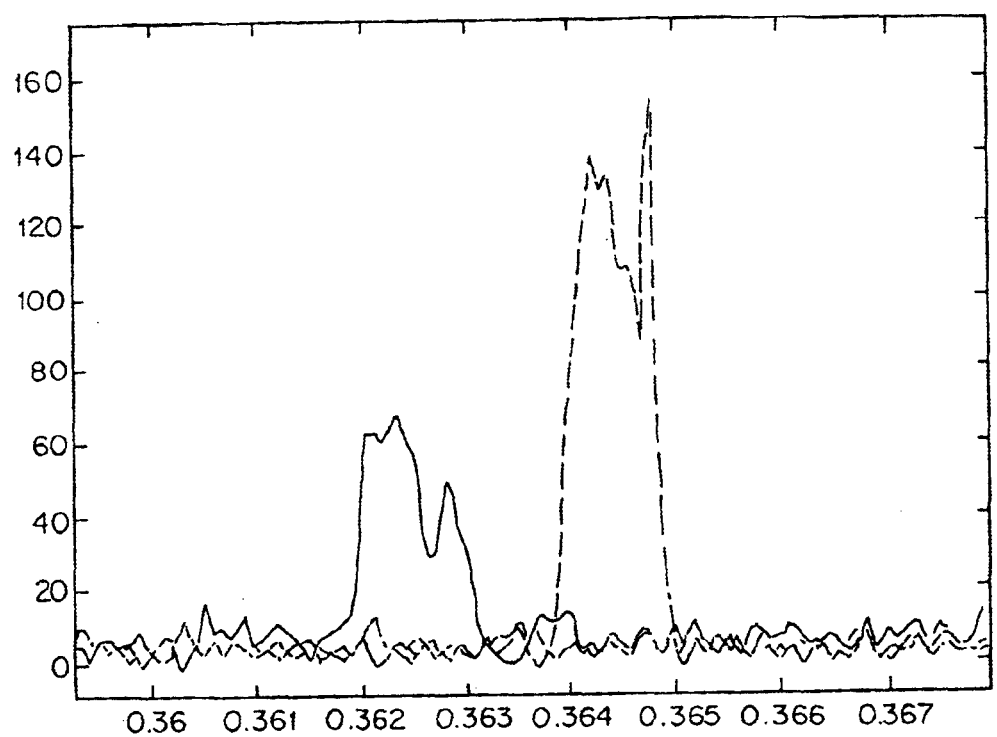
Figure 11C:
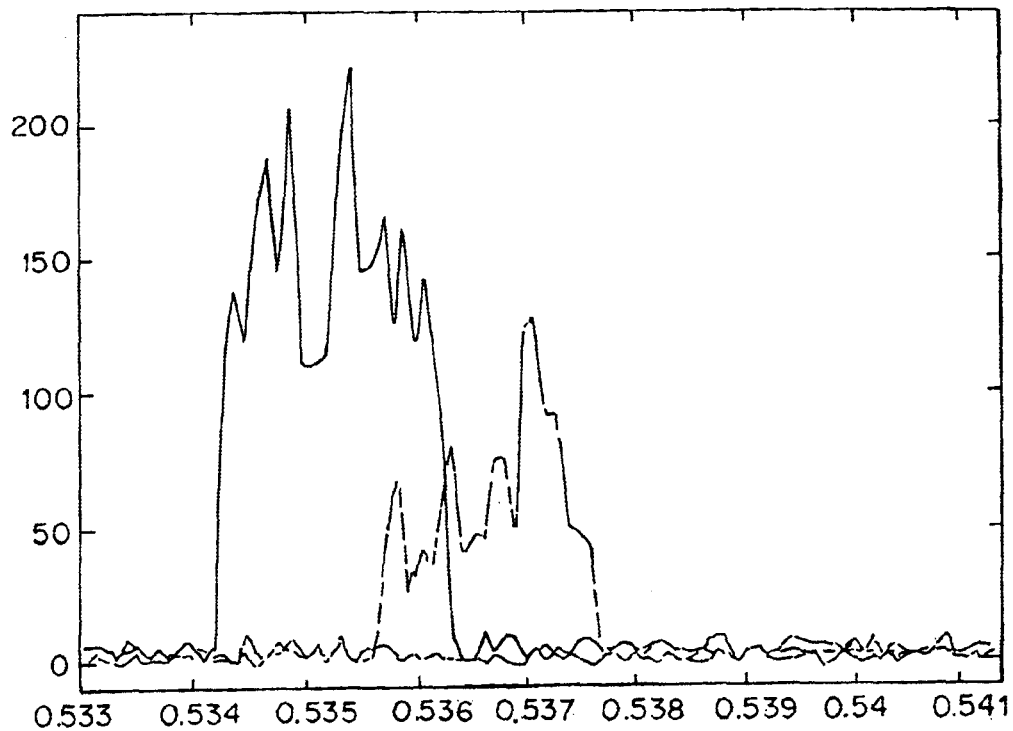

FIGS. 11A–11C show exemplary signal amplitude profiles measured at two detection zones.

Figure 12:
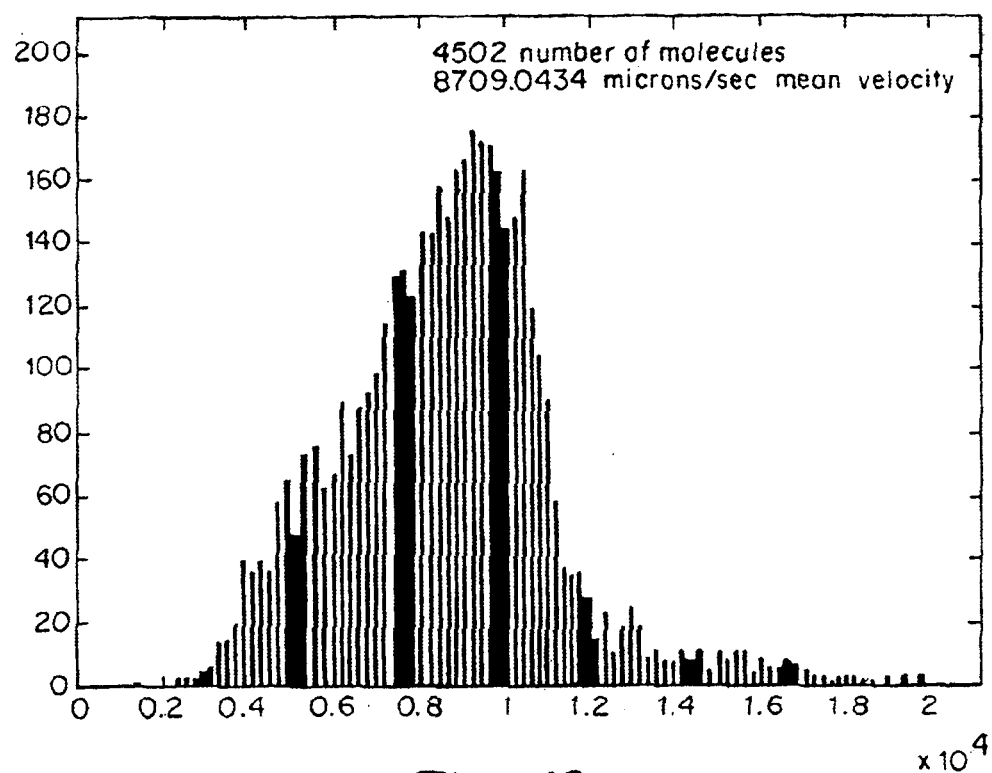
FIG. 12 shows a velocity histogram based upon center-of-mass velocity of a population of λ-DNA molecules measured using one method of the invention.

FIG. 12 shows a velocity histogram based upon the center-of-mass velocity of the detected λ-DNA molecules.

Figure 13:
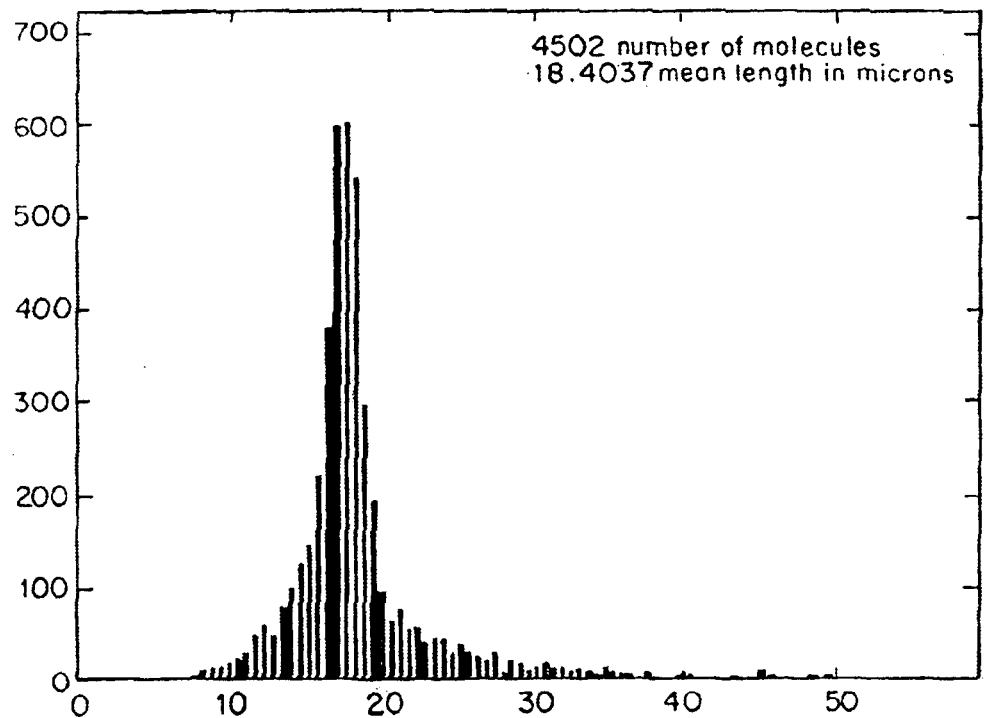
FIG. 13 shows a length histogram of a population of λ-DNA molecules measured using one method of the invention.

FIG. 13 shows a length histogram of the of λ-DNA molecules.

Equivalents

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method for determining velocity of an elongated polymer through a device, the method comprising:
    defining at least one detectable region on the polymer;
    causing relative movement of the elongated polymer through a plurality of linearly sequential detection zones of a device, each separated a predetermined distance, to cause interactions between the detectable region and the detection zones, thereby producing a plurality of signal amplitude profiles, each signal amplitude profile being produced at a different detection zone and comprising data acquired before, during and after each interaction;
    measuring each of the signal amplitude profiles in a time-correlated manner; and
    analyzing the time-correlated measurements and the predetermined distance to determine the velocity of the polymer.

2. The method of claim 1, wherein the plurality of linearly sequential detection zones comprises a first detection zone and a second detection zone.

3. The method of claim 2, wherein a first signal amplitude profile is measured at the first detection zone and a second signal amplitude profile is measured at the second detection zone.

4. The method of claim 3, wherein each signal amplitude profile has a center-of-mass, a contour center, a leading edge, and a leading-edge-rise-time.

5. The method of claim 4, wherein the velocity of the elongated polymer is a center-of-mass velocity determined by the steps of:
    determining the time interval between detection of the center-of-mass in the first signal amplitude profile and the center-of-mass in the second signal amplitude profile; and
    dividing the predetermined distance between the detection zones by the time interval.

6. The method of claim 4, wherein the velocity of the elongated polymer is a center-to-center velocity determined by the steps of:
    determining the time interval between detection of the contour center of the first signal amplitude profile and the contour center of the second signal amplitude profile; and
    dividing the predetermined distance between the detection zones by the time interval.

7. The method of claim 4, wherein the velocity of the elongated polymer is an edge-to-edge velocity determined by the steps of:
    determining the time interval between detection of the leading edge of the first signal amplitude profile and the leading edge of the second signal amplitude profile; and
    dividing the predetermined distance between the detection zones by the time interval.

8. The method of claim 4, wherein the velocity of the elongated polymer is a rise time velocity determined by the steps of:

determining the time interval between detection of the leading-edge-rise-tiwe in the first signal amplitude profile and the leading-edge-rise-time in the second signal amplitude profile; and dividing the predetermined distance between the detection zones by the time interval.

9. The method of claim 1 wherein the detectable region is intrinsically detectable.

10. The method of claim 1 wherein the detectable region is extrinsically detectable.

11. The method of claim 1 wherein the detectable region is detected by measurement of a physical quantity selected from a group comprising of electromagnetic radiation, electrical conductance, thermal conductance, and radioactivity.

12. The method of claim 1 wherein the detectable region is detected by direct or indirect measurement of fluorescent radiation.

13. A method for determining the length of an elongated polymer, the method comprising:

defining a detectable region along the entire length of the polymer;

causing relative movement of the elongated polymer through first and second detection zones, the zones being linearly spaced apart by a predetermined distance;

measuring a time interval between detection of the elongated polymer at the first detection zone and detection of the elongated polymer at the second detection zone;

dividing the predetermined distance between the first and second detection zones by the time interval of step c) to determine the velocity of the polymer;

measuring, at one of the detection zones, a time interval during which the polymer is detected; and multiplying the velocity of step d) by the time interval of step e) to determine the length of the elongated polymer.

14. A method for determining the distance between first and second landmarks on an elongated polymer, the method comprising:

providing first and second landmarks on an elongated polymer;

causing relative movement of the elongated polymer through first and second detection zones, the zones being linearly spaced apart by a predetermined distance, to cause detection of the first and second landmarks at the first detection zone and detection of the first and second landmarks at the second detection zone;

measuring the time interval between detection of one landmark at the first detection zone and detection of that same landmark at the second detection zone;

dividing the predetermined distance between the first and second detection zones by the time interval of step c) to determine the velocity of the polymer;

measuring the time interval between detection of the first landmark at one detection zone and detection of the second landmark at that same detection zone; and multiplying the velocity of step d) by the time interval of step e) to determine the distance between the first and second landmarks.

15. The method of claim 1, wherein the elongated polymer comprises an elongated DNA molecule.

16. The method of claim 13, wherein the elongated polymer comprises an elongated DNA molecule.

17. The method of claim 14, wherein the elongated polymer comprises an elongated DNA molecule.

18. The method of claim 1, wherein the elongated polymer includes fluorescent labels, and further wherein the measurements are measurements of fluorescence intensity.

19. The method of claim 13, wherein the elongated polymer includes fluorescent labels, and further wherein detection of the elongated polymer comprises detection of fluorescent energy.

20. The method of claim 14, wherein each of the landmarks comprises a fluorescent label, and further wherein detection of the landmarks comprises detection of fluorescent energy.

21. The method of claim 20, wherein the first landmark is labeled with a first fluorescent tag and the second landmark is labeled with a second fluorescent tag, and further wherein the first and second fluorescent tags emit fluorescent energy at different and distinguishable wavelengths.

22. The method of claim 1, wherein the detection zones are positioned along an elongation channel through which the polymer is caused to travel.

23. The method of claim 13, wherein the detection zones are positioned along an elongation channel through which the polymer is caused to travel.

24. The method of claim 14, wherein the detection zones are positioned along an elongation channel through which the polymer is caused to travel.

* * * * *

UNITED STATES PATENT AND TRADEMARK OFFICE
CERTIFICATE OF CORRECTION

PATENT NO.   : 6,927,065 B2
DATED        : August 9, 2005
INVENTOR(S)  : Chan et al.

It is certified that error appears in the above-identified patent and that said Letters Patent is hereby corrected as shown below:

Column 21,
Line 2, "tiwe" should read -- time --.

Signed and Sealed this

Twenty-seventh Day of September, 2005

JON W. DUDAS
*Director of the United States Patent and Trademark Office*